US012661518B2

(12) United States Patent
Harlev et al.

(10) Patent No.: US 12,661,518 B2
(45) Date of Patent: Jun. 23, 2026

(54) SYSTEMS FOR TISSUE STIMULATION AND ASSOCIATED METHODS

(71) Applicant: Affera, Inc., Newton, MA (US)

(72) Inventors: Doron Harlev, Watertown, MA (US);
Paul B. Hultz, Watertown, MA (US);
Robert Alan Mest, Long Beach, CA (US)

(73) Assignee: AFFERA, INC., Newton, MA (US)

( * ) Notice: Subject to any disclaimer, the term of this patent is extended or adjusted under 35 U.S.C. 154(b) by 427 days.

(21) Appl. No.: 18/006,368

(22) PCT Filed: Aug. 6, 2021

(86) PCT No.: PCT/US2021/045085
§ 371 (c)(1),
(2) Date: Jan. 20, 2023

(87) PCT Pub. No.: WO2022/032183
PCT Pub. Date: Feb. 10, 2022

(65) Prior Publication Data
US 2023/0264031 A1      Aug. 24, 2023

Related U.S. Application Data

(60) Provisional application No. 63/062,298, filed on Aug. 6, 2020.

(51) Int. Cl.
*A61N 1/37*       (2006.01)
*A61N 1/36*       (2006.01)
*A61N 1/05*       (2006.01)

(52) U.S. Cl.
CPC ........... *A61N 1/371* (2013.01); *A61N 1/3606* (2013.01); *A61N 1/056* (2013.01)

(58) Field of Classification Search
CPC .. A61N 1/371; A61N 1/3606; A61B 5/02028;
A61B 5/4041
See application file for complete search history.

(56) References Cited

U.S. PATENT DOCUMENTS 4,708,145 A      11/1987  Tacker, Jr. et al.
5,010,894 A  *   4/1991  Edhag .................. A61N 1/0563
607/128

(Continued)

OTHER PUBLICATIONS

ISA, "PCT Application No. PCT/US21/45085, International Search Report and Written Opinion mailed Jan. 20, 2022", 12 pages.

(Continued)

*Primary Examiner* — William J Levicky
(74) *Attorney, Agent, or Firm* — Tarolli, Sundheim, Covell & Tummino LLP

(57)                ABSTRACT

Devices, systems, and methods for pacing tissue are disclosed herein. In some embodiments, the devices, systems, and methods position a tip section of a catheter adjacent tissue within an anatomical structure. The tip section is attached to a distal end portion of a catheter shaft, has a maximum radial dimension that is larger than a maximum radial dimension of the catheter shaft, and includes a plurality of electrodes spatially distributed about the tip section. The devices, systems, and methods further select one or more groupings of individual ones of the plurality of electrodes and deliver stimulating energy to or through the adjacent tissue via the selected groupings of electrodes. The stimulating energy is sufficient to activate nerve tissue proximate the tip section but is insufficient to ablate the adjacent tissue. In this manner, devices, systems, and methods disclosed herein can be used to locate nerve tissue proximate the tip section.

23 Claims, 9 Drawing Sheets

(56)            References Cited

U.S. PATENT DOCUMENTS

| | | | |
|---|---|---|---|
| 5,376,105 A | 12/1994 | Hedberg | |
| 5,584,885 A | 12/1996 | Hirschberg et al. | |
| 5,995,871 A * | 11/1999 | Knisley | A61N 1/3622 |
| | | | 607/15 |
| 6,190,382 B1 | 2/2001 | Ormsby et al. | |
| 6,292,695 B1 * | 9/2001 | Webster, Jr. | A61N 1/0563 |
| | | | 607/148 |
| 6,640,135 B1 | 10/2003 | Salo et al. | |
| 7,043,301 B1 * | 5/2006 | Kroll | A61N 1/3627 |
| | | | 607/9 |
| 9,814,521 B2 | 11/2017 | Geistert | |
| 2002/0022866 A1 * | 2/2002 | Borkan | A61N 1/36067 |
| | | | 607/59 |
| 2005/0154420 A1 | 7/2005 | Diaz et al. | |
| 2017/0238807 A9 | 8/2017 | Vertikov | |
| 2018/0214202 A1 | 8/2018 | Howard et al. | |
| 2020/0205890 A1 | 7/2020 | Harlev et al. | |

OTHER PUBLICATIONS

ISA, "PCT Application No. PCT/US21/14216, International Search Report and Written Opinion mailed Jun. 3, 2021". 18 pages.

* cited by examiner

| | Pulse 1 | Pulse 2 | Pulse 3 | Pulse 4 | Pulse 5 | Pulse 6 |
|---|---|---|---|---|---|---|
| 850 | + | | | | | |
| 835 | | - | | | | |
| 851 | - | | | | | |
| 852 | | | | | | |
| 826t | | + | | | | |
| 826d1 | | | + | | | |
| 826d2 | | | | + | | |
| 826d3 | | | | | + | |
| 826d4 | | | | | | + |
| 826p1 | | | | | - | |
| 826p2 | | | | | | - |
| 826p3 | | | - | | | |
| 826p4 | | | | - | | |

Time →

+: connected to source (positive)
-: connected to sink (negative)

SYSTEMS FOR TISSUE STIMULATION AND ASSOCIATED METHODS

CROSS-REFERENCE TO RELATED APPLICATION(S)

This application is a National Stage Entry under 35 U.S.C. § 371 of International Application No. PCT/US2021/045085, filed Aug. 6, 2021, which claims the benefit of U.S. Provisional Patent Application No. 63/062,298, filed Aug. 6, 2020, and entitled "SYSTEMS FOR TISSUE STIMULA-TION AND ASSOCIATED METHODS", the entire contents of which are hereby incorporated herein by reference.

BACKGROUND

Cardiac arrhythmias are usually initiated and/or maintained by specific regions of cardiac tissue. For example, fibrotic or scarred tissue can sometimes cause conduction delay or exhibit automaticity and be responsible for arrhythmia. A minimally-invasive catheter can be used in a patient's heart to treat certain arrhythmias. For example, a minimally-invasive catheter can be used to deliver therapy to the wall of the patient's heart. In this scenario, the catheter can be used to form one or more lesions on the wall of the patient's heart by applying energy (e.g., electrical energy) to the wall. The applied energy damages tissue at the treatment site(s), terminating the tissue's electrical activity. In turn, abnormal electrical signals can be prevented from propagating through the treated tissue, thereby preventing arrhythmias.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

A. Overview

Figure 1A:
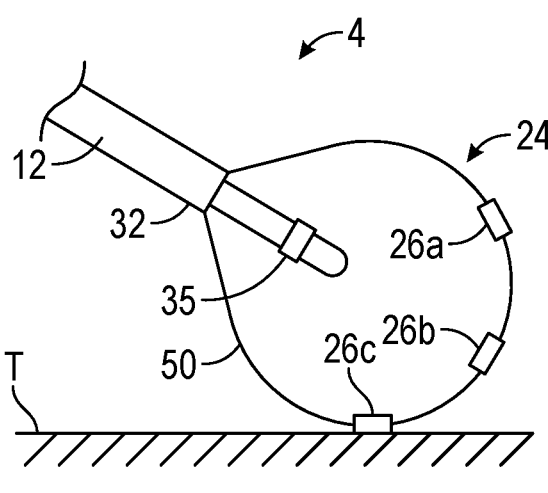
FIGS. 1A-1C are schematic representations of a tip section of a pacing medical device.

As discussed above, specific regions of cardiac tissue can initiate or maintain cardiac arrhythmias. For example, fibrotic or scarred tissue can sometimes cause conduction delay, exhibit automaticity, and/or support reentry and be responsible for arrhythmia. Certain nerve tissues, such as ganglionated plexi on the epicardial surface of the heart, have also been shown to contribute to arrhythmias. A minimally-invasive catheter can be used to apply energy to tissue to damage the tissue and terminate its electrical activity. In turn, abnormal electrical signals can be prevented from propagating through the treated tissue, thereby preventing arrhythmias.

To treat arrhythmias, however, it is often desirable to treat only problematic tissue. That is, it is often desirable to identify and treat tissue that initiates or maintains cardiac arrhythmias, whereas it is often undesirable to treat cardiac or nerve tissue that does not contribute to an arrhythmia. Specifically, it may be desirable to (i) create an electrical block across an isthmus that may support conduction delay or reentry, (ii) isolate tissue where conduction delay, automaticity, or reentry is observed or expected, or (iii) specifically target a focal source of arrhythmia. In these and other cases, it may be undesirable to ablate tissue that does not contribute to or sustain the arrhythmia. For example, ablation of certain nerve tissues proximate sites in the heart where energy is applied can lead to several patient health complications. As a specific example, the left and right phrenic nerves are typically located in close proximity to the right atrium, the right superior pulmonary vein, the superior vena cava, and the left atrial appendage. Thus, it is possible to damage phrenic nerves during ablations procedures, such as during pulmonary vein and superior vena caval isolation procedures. Damage to a phrenic nerve can lead to patient health complications, including diaphragmatic paresis and respiratory insufficiency, among others.

Unfortunately, locations of the phrenic nerves and other nerve tissue relative to potential treatment sites are often not immediately apparent. For this reason, pacing systems are often employed to locate nerve tissue proximate a potential treatment site before applying ablation treatment. Pacing systems include electrodes that can be used to apply energy to stimulate nerve tissue. Nerve tissue stimulation can be detected, for example, by muscle stimulation and resulting movement. When nerve tissue (e.g. the phrenic nerve) is detected proximate a potential treatment site, a physician may decide to deliver therapy elsewhere. A physician may also use pacing systems to locate nerve or cardiac tissue intended for treatment or as a target for programmed stimulation, such as (i) ganglionated plexi, (ii) sites of conduction delay, automaticity, or reentry, or (iii) sites of breakthrough in an ablation lesion.

Most conventional pacing systems include a small number of stimulating electrodes (e.g., one or two) that are tightly spaced relative to one another and/or that cover a majority of the surface area of a tip section of a pacing catheter. As such, the stimulating electrodes on most conventional pacing systems are expected to contact cardiac tissue regardless of the orientation at which the tip section contacts the cardiac wall. Therefore, these conventional pacing systems are able to pace without concern that the stimulating electrodes are in contact with cardiac tissue.

Figure 1B:
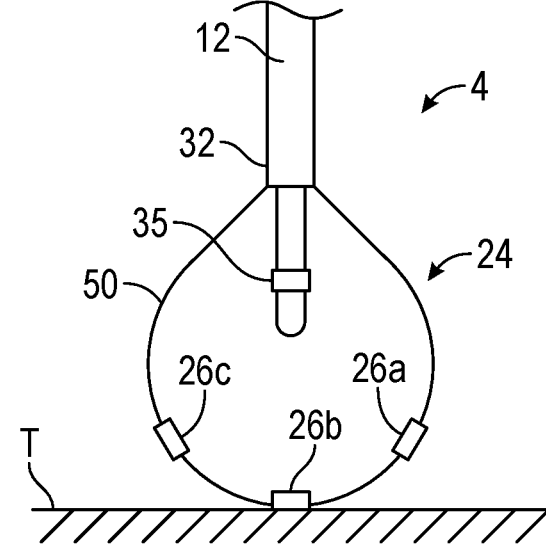
Figure 1C:
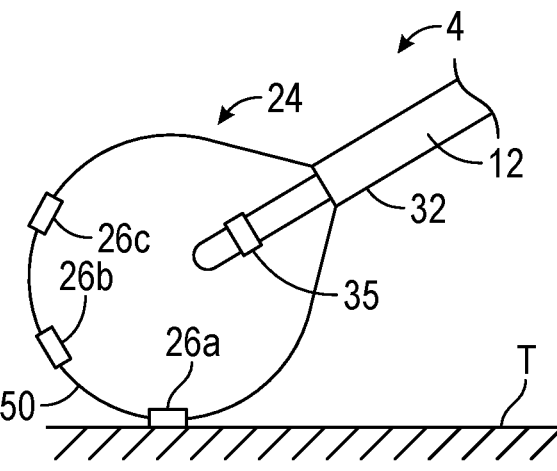

In contrast, some pacing systems (including the system disclosed herein, basket pacing systems, and/or flower pacing systems, among others) include a relatively larger number of (e.g., more than two) electrodes (a) that are spatially distributed about a tip section of a pacing catheter and (b) that individually cover only a small portion of the tip section's surface area. For example, FIGS. 1A-1C illustrate a pacing catheter 4 having a tip section 24 at a distal end portion 32 of a catheter shaft 12. The tip section 24 includes a support structure 50, a plurality of stimulating electrodes 26 (individually labeled as 26a, 26b, and 26c), and a center electrode 35. In operation, various combinations of the electrodes 26 and/or the center electrode 35 are used to pace tissue T by configuring one electrode of a combination as a source and the other electrode of the combination as a sink using a power source, generator, or stimulator.

The tip section 24 is shown interacting with tissue T at various orientations in FIGS. 1A-1C, and a different one of the plurality of stimulating electrodes 26 contacts the tissue T in each of the illustrated orientations. As such, different ones of the stimulating electrodes 26 are expected to contact the tissue T depending on (i) the shape and/or other characteristics of the tissue T and/or (ii) the orientation of interaction between the tip section 24 and the tissue T. Therefore, it is often not immediately apparent which combination of the plurality of stimulating electrodes 26 and/or the center electrode 35 is best for an operator to pace at any given time. Determining the best combination of the plurality of electrodes 26 and/or the center electrode 35 to pace can be difficult, time-consuming, impractical, and/or prone to error. Furthermore, it may be difficult, time-consuming, impractical, and/or error-prone to apply the selected configuration of the plurality of electrodes 26 and/or the center electrode 35 to the power source or stimulator. In addition, the best combination of electrodes to pace may change within a short amount of time, especially while dragging the tip section 24 along the tissue T and/or otherwise moving the tip section 24 to different positions/orientations. Moreover, pacing the wrong combination of the stimulating electrodes 26 (e.g., electrodes 26a and/or 26b in FIG. 1A) and/or the center electrode 35 could result in (a) failure to identify tissue that initiates or maintains a cardiac arrhythmia, potentially hindering appropriate treatment, and/or (b) concluding that no nerve tissue is proximate a paced area, potentially leading to unintentionally damaging nerve tissue during a subsequent ablation procedure.

To address these concerns, the present disclosure is directed to pacing devices, systems, and methods that simultaneously or sequentially deliver stimulating energy to tissue via various combinations of electrodes on a tip section of a catheter and over a short period of time (e.g., less than the refractory period of the tissue). In some embodiments, the various combinations of electrodes are selected to cover all or a significant portion of the surface area of the tip section. In these and other embodiments, the various combinations of electrodes are selected to include electrodes currently in contact with the tissue. In these and still other embodiments, the various combinations of electrodes are selected to include unipolar, bipolar, and/or near-unipolar combinations of electrodes, and/or combinations of electrodes having different sizes. In this manner, the pacing devices, systems, and associated methods of the present disclosure are configured to pace using several different combinations of electrodes, thereby (i) covering a large number of potential catheter-tissue orientations and interactions and (ii) obviating the practice of an operator selecting an appropriate combination of electrodes and/or applying the selected configuration to the power source or stimulator. In turn, the pacing devices, systems, and associated methods of the present disclosure are expected to provide rapid and accurate identification of tissue that initiates or maintains cardiac arrhythmias and/or to provide rapid and accurate indications of whether nerve tissue is positioned proximate the tip section.

Specific details of several embodiments of the present technology are described herein with reference to FIGS. 1A-10. Although many of the embodiments are described with respect to devices, systems, and methods of applying energy to tissue in a heart of a patient to determine the locations of nerve tissue proximate a potential treatment site, other applications and other embodiments in addition to those described herein are within the scope of the present technology. For example, unless otherwise specified or made clear from context, the devices, systems, and methods of the present technology can be used for any of various medical procedures, such as procedures performed on a hollow anatomical structure of a patient, and, more specifically, in a hollow anatomical structure in which direct visual access to the medical procedure is impractical and/or is improved by the use of a model of the anatomical structure. Thus, for example, the systems, device, and methods of the present technology can be used to facilitate visualization of a medical device inserted into a heart cavity as part of a medical treatment associated with diagnosis, treatment, or both of a cardiac condition. Additionally, or alternatively, the devices, systems, and methods of the present technology can be used in one or more medical procedures associated within interventional pulmonology, brain surgery, or sinus surgery (e.g., sinuplasty).

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a clinician, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in an anatomical chamber. As used herein, the term "patient" should be considered to include human and/or non-human (e.g., animal) patients upon which a medical procedure is being performed.

B. Selected Embodiments of Cardiac Pacing Devices, Systems, and Methods

1. Cardiac Pacing Devices and Systems

Figure 2:
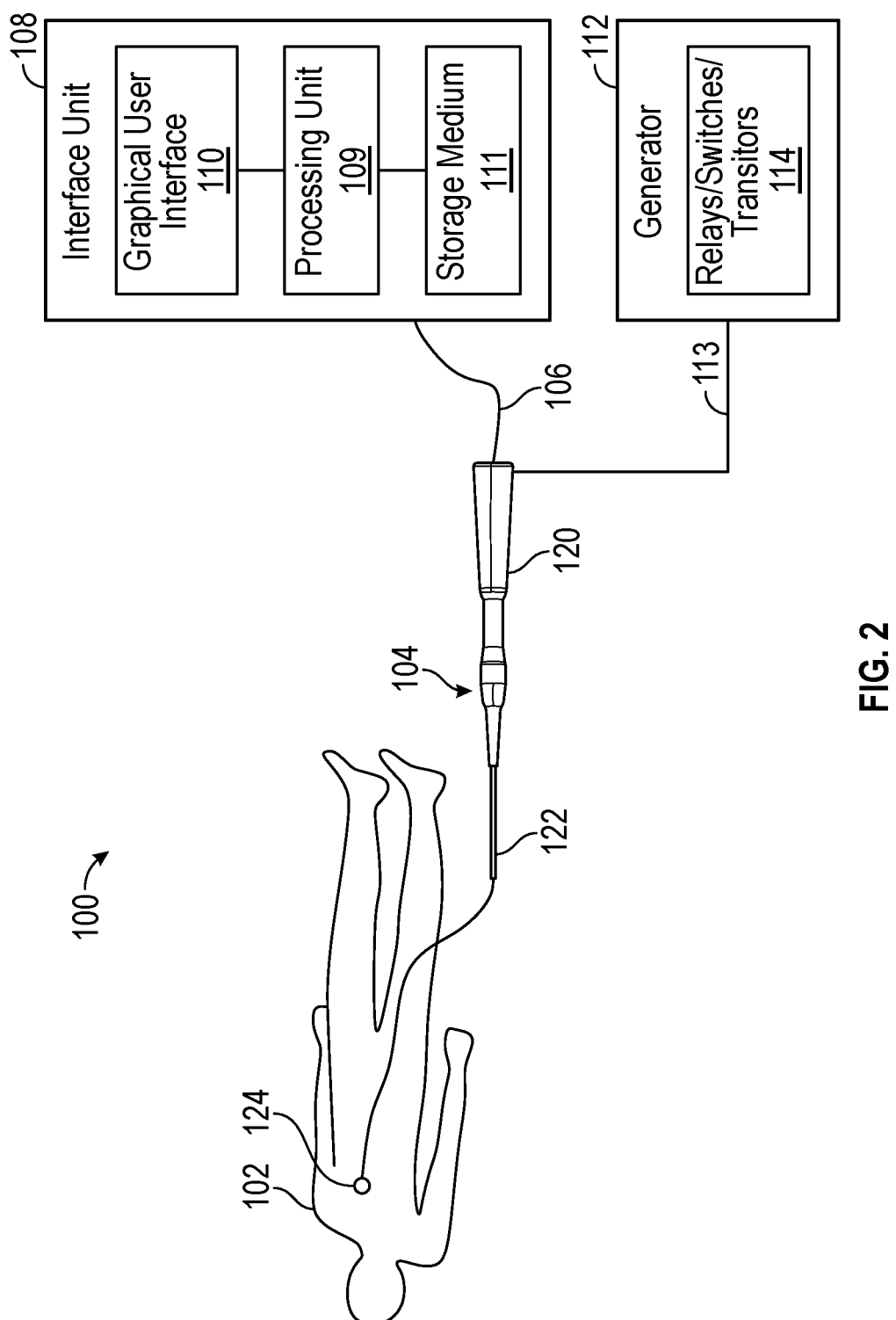
FIG. 2 is a schematic representation of a system configured in accordance with various embodiments of the present technology.

FIG. 2 is a schematic representation of a system 100 configured in accordance with an embodiment of the present technology. In the arrangement shown in FIG. 2, the system 100 is being used to perform a medical procedure (e.g., a diagnosis procedure, an ablation treatment, or both) on a human patient 102. The system 100 can include a medical device 104 connected via an extension cable 106 to an interface unit 108. The interface unit 108 (e.g., a catheter interface unit) can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109. The storage medium 111 can have stored thereon computer executable instructions for causing the one or more processors of the processing unit 109 to carry out one or more portions of the various methods described herein, unless otherwise indicated or made clear from context. The medical device 104 can further be connected via an extension cable 113 to an energy generator 112. The generator 112 can be configured to deliver electrical energy (e.g., stimulating energy, ablative energy, radiofrequency energy, pulsed field energy, electroporation energy, etc.) to a tip section 124 of the medical device 104. As described in greater detail below, the generator 112 can include one or more relays, switches, and/or transistors 114 for configuring one or more combinations of electrodes on a tip section 124 of the medical device 104 for energy delivery. For example, the relays, switches, and/or transistors 114 can be used to sequentially configure various electrodes on the tip section 124 as source electrodes and various electrodes on the tip section 124 as sink electrodes (e.g., to deliver stimulating energy to tissue). In some embodiments, the system 100 can include one or more other components, such as a mapping system, a recording system, a fluid pump, and/or one or more electrodes attached to the skin of the patient 102 (e.g., one or more return electrodes, one or more electrodes configured to capture an electrocardiogram of the patient 102, etc.).

As described in further detail below, the graphical user interface 110 can be used as part of diagnosis and/or treatment of tissue of an anatomical structure (e.g., a heart) of the patient 102 by, for example, generating and/or displaying three-dimensional annotations and/or other information relative to the location of the tip section 124 of the medical device 104. The three-dimensional annotations generated and/or displayed in accordance with various embodiments of the present technology can be used alone or in combination with other three-dimensional information, such as with a three-dimensional surface representation of the anatomical structure. In some embodiments, for example, a three-dimensional annotation can represent the current location of the tip section 124 of the medical device 104 within the anatomical structure and/or the location of the tip section 124 within the anatomical structure when nerve tissue was activated and/or when therapy was delivered. In these and other embodiments, three-dimensional annotations can display various information based, at least in part, on signals received from sensors 126 distributed about the tip section 124 of the medical device 104. In this manner, the present technology is expected to provide a physician with improved spatial context for three-dimensional movement and/or proximity of the medical device 104 relative to one or more surfaces of the anatomical structure. As a specific example, generating and/or displaying the three-dimensional annotations and/or other information alone or in combination with the three-dimensional model on the graphical user interface 110 can facilitate three-dimensional movement of the medical device 104 within the anatomical structure to investigate potential treatment sites and/or to create one or more lesions in a desired pattern on one or more surfaces of the anatomical structure represented by the three-dimensional model.

Figure 3:
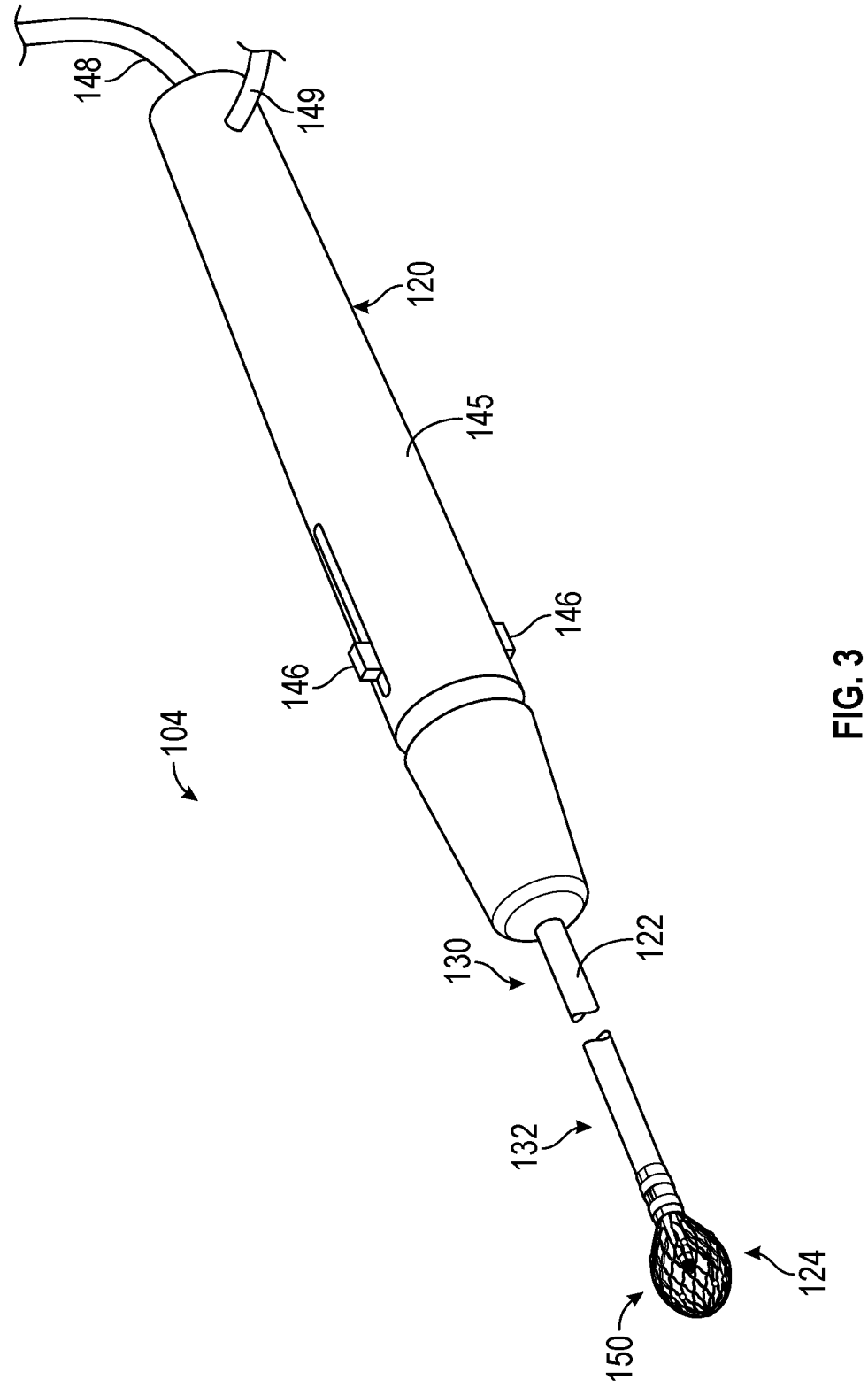
FIG. 3 is a perspective view of an exemplary medical device of the system of FIG. 2 configured in accordance with various embodiments of the present technology.
Figure 4:
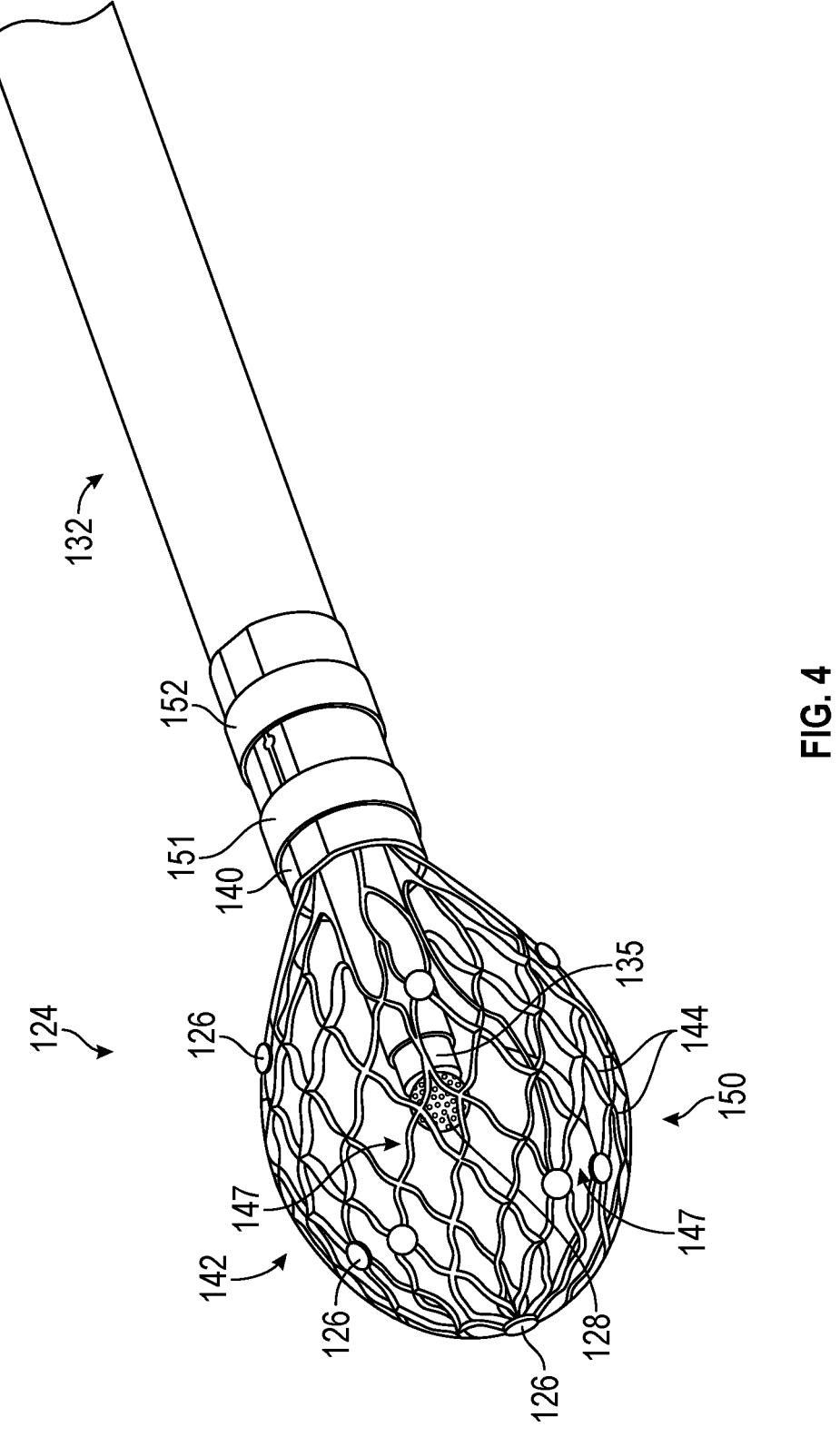
FIG. 4 is a schematic representation of a tip section of the medical device of FIG. 3 and configured in accordance with various embodiments of the present technology.

FIG. 3 is a perspective view of the medical device 104 of the system 100 of FIG. 2, and FIG. 4 is a schematic representation of the tip section 124 of the medical device 104. Referring to FIGS. 2-4 together, the medical device 104 can be any of various different medical devices known in the art (e.g., for diagnosis, treatment, or both). In the illustrated embodiment, for example, the medical device 104 is a catheter. The medical device 104 can include a handle 120, a shaft 122, a tip section 124, and/or a fluid delivery element 128. The handle 120 can be coupled to a proximal end portion 130 of the shaft 122. The tip section 124 and/or the fluid delivery element 128 can be coupled to a distal end portion 132 of the shaft 122 opposite the proximal end portion 130. In some embodiments, the shaft 122 can define a lumen that can be in fluid communication with a fluid pump (not shown). Additionally, or alternatively, the shaft 122 can include electrical wires extending along the shaft 122 to carry energy and/or signals between the tip section 124 and the handle 120.

The handle 120 can include a housing 145 and an actuation portion 146. In use, the actuation portion 146 can be operated to deflect a distal end portion 132 of the shaft to facilitate positioning the tip section 124 into contact with tissue. The handle 120 can further be coupled to a fluid line connector 149 and/or to an electrical connector 148 for delivery of fluid, electrical signals, and/or energy (e.g., electrical energy), respectively, along the shaft 122 to/from the tip section 124 (e.g., to/from an electrode 150 and/or to/from one or more sensors 126 of the tip section 124).

The tip section 124 generally includes any portion of the catheter 104 that directly or indirectly engages tissue for the purpose of diagnosis, treatment, or both and, therefore, can include all manner and type of contact and/or non-contact interaction with tissue known in the art. For example, the tip section 124 can include measurement of electrical signals emanating from tissue and further, or instead, can include contact and/or non-contact interaction with tissue in the form of energy interaction (e.g., electrical energy, ultrasound energy, light energy, and any combinations thereof). Thus, for example, the tip section 124 can deliver energy (e.g., electrical energy) to tissue in the anatomical structure as part of any number of procedures including diagnosis (e.g., mapping, pacing, etc.), treatment (e.g., ablation, electroporation, etc.), or both.

In the illustrated embodiments, the tip section 124 includes a coupling portion 140 and a deformable portion 142. As used herein, the terms "expandable" and "deformable" are used interchangeably, unless otherwise specified or made clear from the context. Thus, for example, it should be understood that the deformable portion 142 is expandable unless otherwise specified. The coupling portion 140 is secured to the distal end portion 132 of the shaft 122, and the deformable portion 142 can extend distally from the coupling portion 140. Two ring electrodes 151 and 152 are positioned about the distal end portion 132 of the shaft 122 proximate the coupling portion 140 and are electrically coupled to the generator 112 (FIG. 2) via one or more wires (not shown) extending along the shaft 122.

The deformable portion 142 of the tip section 124 can be deformed for delivery and expanded within an anatomical structure to have a cross-sectional dimension larger than a cross-sectional dimension of the shaft 122. Further, in an expanded state, the deformable portion 142 of the tip section 124 is deformable upon sufficient contact force with tissue.

As described in greater detail below, the shape and extent of the deformation of the deformable portion can be detected based at least in part on signals received from sensors 126 of the tip section 124. In some embodiments, the deformable portion 142 can be radiopaque such that deformation of the deformable portion 142 as a result of contact with tissue is observable, for example, through X-ray or similar visualization techniques. The detection and/or observation of the deformation of the deformable portion 142 of the tip section 124 can, for example, provide improved certainty that an intended stimulation or treatment is indeed being provided to tissue. It should be appreciated that improved certainty of positioning of an electrode 150 of the tip section 124 with respect to tissue can reduce the likelihood of gaps in a lesion pattern during treatment and, also or instead, can reduce the time and number of lesions otherwise required to avoid gaps in a lesion pattern.

The deformable portion 142 of the tip section 124 can include an electrode 150. In some embodiments, the deformable portion 142 can include struts 144 joined together to form the electrode 150. In the illustrated embodiment, the struts 144 are joined to collectively define a plurality of cells 147. In other embodiments, however, the struts 144 can be joined in accordance with methods known in the art. Additionally, or alternatively, at least some of the struts 144 can be coupled to the coupling portion 140 of the tip section 124 to secure the deformable portion 142 to the distal end portion 132 of the shaft 122. The struts 144 can be moveable relative to one another. More specifically, the struts 144 can be flexible to one another such that the deformable portion 142 can move between a compressed state, in the presence of external force, and an uncompressed state, in the absence of external force (e.g., in embodiments where the deformable portion 142 is self-expandable). In the uncompressed state of the deformable portion 142, the ablation electrode 150 can be bulbous. For example, in the uncompressed state, the deformable portion 142 can be a shape having symmetry in a radial direction and/or an axial direction relative to the catheter shaft 122. For example, in the uncompressed state the deformable portion 142 can be an ellipsoidal shape such as, for example, a substantially spherical shape. Additionally, or alternatively, in the uncompressed state, the deformable portion 142 can be a symmetric shape (e.g., a substantially ellipsoidal shape or another similar shape contained between a first radius and a perpendicular second radius, the first radius and the second radius within 30 percent of one another in magnitude). Symmetry of the deformable portion 142 can, for example, facilitate symmetric delivery of ablation energy to the tissue in a number of orientations of the deformable portion 142 relative to the tissue being ablated. In general, the struts 144 of the electrode 150 can be dimensioned and arranged relative to one another for delivery of substantially uniform current density through the deformable portion 142 of the tip section 124. The struts 144 can be electrically coupled to the electrical connector 148 (e.g., via one or more wires (not shown) extending along the shaft 122).

The electrode 150 is a continuous structure about the deformable portion 142 that acts as one electrode in a monopolar electrode configuration. It should be appreciated, however, that the electrode 150 can include electrically isolated portions about the deformable portion 142 such that the electrode 150 includes two electrodes of a bipolar electrode configuration.

In use, energy (e.g., electrical energy, radiofrequency (RF) energy, pulsed field (PF) energy, etc.) can be delivered to the electrode 150 to stimulate tissue (e.g., in contact with the electrode 150). For example, as described in greater detail below, the electrode 150 can be grouped with one or more other electrodes on the tip section 124 of the medical device 104 to deliver bipolar, unipolar, and/or near-unipolar stimulating energy to tissue. Such energy delivery can be used to activate and/or locate cardiac and/or nerve tissue positioned proximate the tip section 124 of the medical device 104 as part of a pacing operation (e.g., prior to treating tissue).

Additionally, or alternatively, energy (e.g., electrical energy, RF energy, PF energy, etc.) can be delivered to the electrode 150 to ablate or otherwise treat (e.g., via thermal ablation or irreversible electroporation) tissue (e.g., in contact with the electrode 150). As compared to smaller electrodes, the electrode 150 can provide wider lesions, facilitating the creation of a pattern of overlapping lesions (e.g., reducing the likelihood of arrhythmogenic gaps, and reducing the time and number of lesions required for an overlapping pattern, or both). Additionally, or alternatively, the larger electrode 150 can facilitate the delivery of more power for providing wider and deeper lesions.

In these and other embodiments, the electrode 150 can be an electroporation electrode configured to apply one or more electrical pulses to cells of tissue. For example, the catheter 104 can be configured to apply pulsed field energy (e.g., reversible electroporation, irreversible electroporation, pulsed electrical fields, etc.) and/or another form of energy to tissue at a treatment site via the electrode 150 of the tip section 124. As a more specific example, the catheter 104 can be configured to deliver monophasic or biphasic pulses with high voltage (e.g., between about 500 volts and 4000 volts) and short duration (e.g., between 100 nanoseconds and 200 microseconds) to the electrode 150.

Additionally, or alternatively, the catheter 104 can be configured to deliver various forms of pulse trains of energy to tissue at a treatment site via the electrode 150 of the tip section 124. For example, the catheter 104 can deliver energy to tissue either continuously or as a train of tightly (e.g., temporally) spaced pulses followed by a suspension period during which no energy is delivered to the tissue. At the end of the suspension period, the catheter 104 can again deliver energy to tissue either continuously or as a train of tightly spaced pulses followed by another suspension period. The catheter 104 can repeat this cycle as needed. In still other embodiments, the catheter 104 can vary the amount of current delivered during either continuous energy delivery or during delivery of different pulses (e.g., pulses of a pulse train).

As best seen in FIG. 4, the deformable portion 142 of the electrode 150 can envelop/surround the fluid delivery element 128. In some embodiments, the fluid delivery element 128 includes a stem and bulb. The bulb of the fluid delivery element 128 can define one or more holes in fluid communication with the stem, and the stem can be coupled to the distal end portion 132 of the shaft 122 and can be in fluid communication with the fluid line connector 149 via the lumen of the shaft 122 and the handle 120. Accordingly, fluid can pass through the lumen defined by the shaft 122, through the stem, and can exit the fluid delivery element 128 through the holes defined by the bulb.

The bulb can be substantially hemispherical to facilitate directing fluid toward substantially the entire inner portion of the deformable portion 142. It should be appreciated, however, that the bulb can be any of various different shapes that facilitate multi-directional dispersion of fluid toward the inner portion of the deformable portion 142. Moreover, the fluid delivery element 128 can be spaced relative to the inner portion of the deformable portion 142 such that the holes direct irrigation fluid toward the inner portion of the deformable portion 142 in an expanded state. In particular, given that the deformable portion 142 of the tip section 124 in some embodiments is intended to contact tissue during ablation, the holes can be oriented toward the inner portion of the deformable portion 142 in contact with the tissue. In certain implementations, the holes can be spaced circumferentially about and axially along the fluid delivery element 128. For example, the holes can be spatially distributed along the bulb with at least a portion of the holes arranged to direct fluid in a distal direction with respect to the tip section 124 and at least a portion of the holes arranged to direct irrigation fluid in a proximal direction with respect to the tip section 124. More generally, the holes can be distributed to produce a relatively uniform dispersion of fluid along the inner portion of the deformable portion 142 enveloping the fluid delivery element 128. Directing the fluid toward the deformable portion 142 of the tip section 124 in this way can, for example, reduce the likelihood of unintended tissue damage resulting from an ablation treatment.

The stem of the fluid delivery element 128 can further include a center electrode 135 disposed thereabout. In some embodiments, for example, the center electrode 135 can be directly or indirectly coupled to the distal end portion 132 of the catheter shaft 122. The fluid delivery element 128 can be one or both of electrically and thermally isolated from the center electrode 135. In such instances, the fluid delivery element 128 can be a grounding electrode to reduce noise, measurement error, or both.

As shown in FIG. 4, the tip section 124 and/or the deformable portion 142 can include one or more electrodes or sensors 126. For example, the tip section 124 can include one or more of electrodes, thermistors, ultrasound transducers, optical fibers, image sensors, and/or other types of sensors. Sensors 126 can be mounted about (e.g., along) the deformable portion 142 of the tip section 124 (e.g., mounted onto one of the struts 144 of the deformable portion 142) and can be electrically insulated from the electrode 150. In general, the sensors 126 can be positioned along one or both of the inner portion and the outer portion of the deformable portion 142. For example, sensors 126 can extend through a portion of the deformable portion 142. Such positioning of the sensors 126 through a portion of the deformable portion 142 can facilitate measuring conditions along the outer portion and the inner portion of the electrode 150 and/or of the deformable portion 142. As a specific example, one or more of the sensors 126 can include a flexible printed circuit, a thermistor secured between portions of the flexible printed circuit, and a termination pad opposite the thermistor. A sensor 126 can be mounted on the deformable portion 142 of the tip section 124 with the thermistor disposed along an outer portion of the deformable portion 142 and the termination pad disposed along the inner portion of the deformable portion 142. In certain instances, the thermistor can be disposed along the outer portion to provide an accurate indication of tissue temperature.

The sensors 126 can be substantially uniformly spaced from one another (e.g., in a circumferential direction and/or in an axial direction) about the deformable portion 142 when the deformable portion 142 is in an uncompressed state. Such substantially uniform distribution of the sensors 126 can, for example, facilitate determining an accurate deformation and/or temperature profile of the deformable portion 142 during use and/or can facilitate energy delivery to tissue via one or more of the sensors 126 regardless of the orientation at which the tip section 124 interacts with tissue. In the absence of force applied to the deformable portion 142, the sensors 126 on the deformable portion 142 are spaced apart from the center electrode 135 and/or the fluid delivery element 128. In some embodiments, one or more sensors 126 can include a radiopaque portion and/or a radiopaque marker to facilitate visualization (e.g., using fluoroscopy) of the sensor 126 during use.

In these and other embodiments, one or more sensors 126 of the medical device 104 (e.g., of the tip section 124) can further be a magnetic position sensor. The magnetic position sensor can be any of various magnetic position sensors well known in the art and can be positioned at any point along the distal end portion 132 of the shaft 122 and/or at any point along the tip section 124. The magnetic position sensor can, for example, include one or more coils that detect signals emanating from magnetic field generators. One or more coils for determining position with five or six degrees of freedom can be used. The magnetic field detected by the magnetic position sensor can be used to determine the position and/or orientation of the tip section 124 and/or of the distal end portion 132 of the shaft 122 according to one or more methods commonly known in the art such as, for example, methods based on using a magnetic sensor to sense magnetic fields and using a look-up table to determine location of the magnetic position sensor. Accordingly, because the tip section 124 is coupled to the distal end portion 132 of the shaft 122 in a known, fixed relationship to the magnetic position sensor, the magnetic position sensor can also provide the location of the tip section 124. While the location of the tip section 124 is described as being determined based on magnetic position sensing, other position sensing methods can additionally or alternatively be used. For example, the location of the tip section 124 can be additionally, or alternatively, based on impedance, ultrasound, and/or imaging (e.g., real time MRI or fluoroscopy). Furthermore, a location of the tip section 124 should be understood to include, for example, a smoothed and/or filtered position and/or orientation.

In some embodiments, one or more wires (not shown) extend from each sensor 126 along the inner portion of the deformable portion 142 and into the shaft 122. The one or more wires can be in electrical communication with the interface unit 108 (FIG. 2) and/or the generator 112 (FIG. 2) such that each sensor 126 can send energy/electrical signals to and receive energy/electrical signals from the interface unit 108 and/or the generator 112 during use.

In use, the sensors 126 can be used in one or more modes of parameter measurement. For example, the sensors 126 can measure temperature, electrogram characteristics (e.g., amplitude), force, ultrasound, impedance, location (e.g., motion during therapy), shape of the deformable portion 142 (e.g., during deployment or deformation), shape of an anatomical structure, energy (e.g., power, voltage, current, impedance), and/or other parameter measurements. These parameters vary over time, producing time-varying signals that can be measured by the interface unit 108.

In this regard, one or more sensors 126 can act as an electrode (e.g., a surface electrode) to detect electrical activity of an anatomical structure in an area local to the sensor 126. For example, each sensor 126 can form part of an electrode pair useful for detecting contact between each sensor 126 and tissue. For example, electrical energy (e.g., current) can be driven through each sensor 126 and another electrode (e.g., any one or more of various different electrodes described herein), and a change in a measured signal (e.g., voltage or impedance) can be indicative of the presence of tissue. Because the position of the tip section 124 is known, detection of contact through respective measured signals at the sensors 126 can be useful for determining portions of the deformable portion 142 proximate to tissue and/or for determining a shape of an anatomical structure in which the tip section 124 is disposed during the course of a medical procedure.

In one method, the impedance detected by an electrode pair can be detected (e.g., as a signal received by the processing unit 109) when an electrical signal is driven through the electrode pair. The impedance detected for various electrode pairs can be compared to one another and relative distances between the members of each electrode pair determined. For example, if the sensors 126 are identical, each sensor 126 can be driven as part of a respective electrode pair including the fluid delivery element 128 or the center electrode 135. For each such electrode pair, the measured impedance between the electrode pair can be indicative of relative distance between the particular sensor 126 and the fluid delivery element 128 or the center electrode 135 forming the respective electrode pair. In implementations in which the fluid delivery element 128 is stationary while electrical signals are driven through the electrode pairs, the relative distance between each sensor 126 and the fluid delivery element 128 can be further indicative of relative distance between each sensor 126 and each of the other sensors 126. In general, driven electrode pairs with lower measured impedance are closer to one another than those driven electrode pairs with higher measured impedance. In certain instances, electrodes associated with the tip section 124 (e.g., one or more of the sensors 126) that are not being driven can be measured to determine additional information regarding the position of the driven current pair.

The measurements received by the processing unit 109 and associated with the driven current pairs alone, or in combination with the measurements at the sensors 126 that are not being driven, can be fit to a model and/or compared to a look-up table to determine displacement of the deformable portion 142 of the tip section 124. For example, the determined displacement of the deformable portion 142 can include displacement in at least one of an axial direction or a lateral (radial) direction. It should be appreciated that, because of the spatial separation of the current pairs in three dimensions, the determined displacement of the deformable portion 142 can be in more than one direction (e.g., an axial direction, a lateral direction, and combinations thereof). Additionally, or alternatively, the determined displacement of the deformable portion 142 can correspond to a three-dimensional shape of the deformable portion 142.

Based on the determined displacement of the deformable portion 142 of the tip section 124, the processing unit 109 can send an indication of the shape of the deformable portion 142 to the graphical user interface 110. Such an indication of the shape of the deformable portion 142 can include, for example, a graphical representation of the shape of the deformable portion 142 corresponding to the determined deformation, as described in greater detail below with respect to FIGS. 5 and 6.

Figures 8, 9:
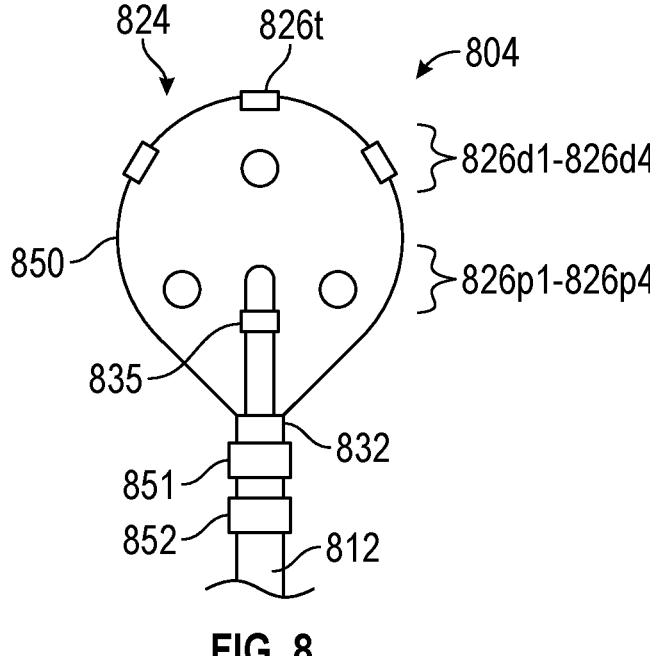
FIG. 8 is a simplified schematic diagram of a tip section of a medical device configured in accordance with various embodiments of the present technology
FIG. 9 is a table illustrating potential electrode pairings of the tip section of FIG. 8 in accordance with various embodiments of the present technology.

In implementations in which the force-displacement response of the deformable portion 142 is reproducible (e.g., as shown in FIG. 9), the processing unit 109 can determine force applied to the deformable portion 142 based on the determined displacement of the deformable portion 142. For example, using a lookup table, a curve fit, or other predetermined relationship, the processing unit 109 can determine the direction and magnitude of force applied to the deformable portion 142 based on the magnitude and direction of the displacement of the deformable portion 142, as determined according to any one or more of the methods of determining displacement described herein. It should be appreciated, therefore, that the reproducible relationship between force and displacement along the deformable portion 142, coupled with the ability to determine displacement using the sensors 126 disposed along the deformable portion 142, can facilitate determining whether an appropriate amount of force is being applied during a medical procedure and, additionally or alternatively, can facilitate determining appropriate energy and cooling dosing for lesion formation.

In use, each sensor 126 can, further or instead, act as an electrode to detect electrical activity of an anatomical structure local to the respective sensor 126, with the detected electrical activity forming a basis for an electrogram with the respective sensor 126 and, further or instead, can provide lesion feedback. The sensors 126 can be arranged such that electrical activity detected by each sensor 126 can form the basis of unipolar electrograms and/or bipolar electrograms.

Additionally, or alternatively, the sensors 126 can cooperate with the center electrode 135 or the fluid delivery element 128, for example, to provide near-unipolar electrograms. For example, a sensor 126 can be disposed along the fluid delivery element 128 and can act as the center electrode 135. Additionally, or alternatively, the fluid delivery element 128 can act as a center electrode itself. In these and still other embodiments, one or more other sensors can be disposed along the fluid delivery element 128, such as one or more image sensors.

Electrical activity detected (e.g., passively detected) by the center electrode 135 and the sensors 126 (acting as surface electrodes) can form the basis of respective electrograms associated with each unique pairing of the center electrode 135 and the sensors 126. For example, in implementations in which there are nine sensors 126, the center electrode 135 can form nine electrode pairs with the sensors 126 which, in turn, form the basis for nine respective electrograms.

An electrogram formed by electrical signals received from each respective electrode pair (i.e., the center electrode 135 and a respective one of the sensors 126) can be generated through any of various different methods. In general, an electrogram associated with a respective electrode pair can be based on a difference between the signals from the electrodes in the pair and, thus more specifically, can be based on a difference between an electrical signal received from the center electrode 135 and an electrical signal received from a respective one of the sensors 126. Such an electrogram can be filtered or otherwise further processed to reduce noise and/or to emphasize cardiac electrical activity, for example.

Because the center electrode 135 remains spaced at an intermediate distance from the sensors 126 and tissue in the range of forces experienced through contact between tissue and the deformable portion 142 of the tip section 124, the electrogram formed from each electrode pair can advantageously be a bipolar or a near-unipolar electrogram. As used herein, a bipolar or a near-unipolar electrogram includes an electrogram formed based on the difference between two electrodes that are spaced less than about 10 mm apart and/or oriented (in the case of a near-unipolar electrogram) such that one of the electrodes remains spaced away from tissue. In certain implementations, in the absence of force applied to the deformable portion 142, the center electrode 135 is spaced apart from the sensors 126 by distance greater than about 2 mm and less than about 6 mm.

The near-unipolar electrograms associated with the center electrode 135 spaced from the sensors 126 can provide certain advantages over unipolar configurations (i.e., configurations having electrode spacing greater than 10 mm) and over bipolar configurations (i.e., configurations having electrode spacing equal to or less than 10 mm but allowing both electrodes to be spaced close to tissue). For example, as compared to unipolar electrograms, the near-unipolar electrograms formed based on signals received from the center electrode 135 and the sensors 126 are less noisy and, additionally or alternatively, less susceptible to far-field interference from electrical activity away from the tissue of interest. Also, as compared to unipolar electrograms, a near-unipolar electrogram does not require a reference electrode on a separate catheter or other device. As a further or alternative example, as compared to bipolar electrograms, a near-unipolar electrogram formed based on signals received from the center electrode 135 and the sensors 126 is generated from an electrode pair with only one electrode in the electrode pair in contact with tissue such that the resulting electrogram waveform arises from one tissue site, making it less complex to interpret. Also, or instead, as compared to bipolar electrograms generated from a pair of electrodes in contact with tissue, the signal of a near-unipolar electrogram formed based on signals received from the center electrode 135 and the sensor 126 in contact with tissue can have a more consistent morphology and/or a larger amplitude at least because the center electrode 135 is always oriented away from tissue as compared to the sensor 126 in the electrode pair touching tissue.

In these and other embodiments, each sensor 126 can be configured to apply energy (e.g., stimulating energy) to tissue. For example, stimulation pulses can be delivered to tissue via one or more of the sensors 126 and/or one or more of the other electrodes described herein to stimulate cardiac tissue and/or nerve tissue (e.g., to pace, map, or otherwise diagnose or treat tissue). As specific examples of stimulating cardiac tissue, stimulation pulses can be delivered to tissue to initiate cardiac activation from a particular location to characterize a resulting activation pattern, to induce an arrhythmia as part of an electrophysiology study, to entrain an existing arrhythmia, and/or to interrupt a cardiac arrhythmia. Additionally, or alternatively, stimulation pulses can be delivered to tissue to detect nerve tissue proximate a potential site for therapy delivery, to modulate nerve activity, and/or to detect specific nerve tissues (e.g., ganglionated plexi, phrenic nerves, etc.).

In some embodiments, the processing unit 109 can control the generator 112 and/or another electrical power source to drive stimulating energy between any number and combination of electrodes associated with the tip section 124. For example, the processing unit 109 can control the generator 112 to drive one or more groupings of the sensors 126, the ablation electrode 150, the irrigation element 128, the center electrode 135, and/or the ring electrodes 151 and/or 152. Additionally, or alternatively, multiple pairs of electrodes can be driven either simultaneously or sequentially (e.g. in a multiplexed manner using time division). The stimulation energy can be any of various, different forms, including, for example, pulses of a prescribed current or a prescribed voltage.

As discussed above, the medical device 104 includes several electrodes spatially distributed about the tip section 124 and that individually cover only a small portion of the tip section's surface area. In operation, various combinations of the electrodes of the tip section 124 can be used to pace tissue within an anatomical structure of the patient 102 by configuring at least one electrode of a combination as a source and/or one or more other electrodes of the combination as a sink. Different combinations of the electrodes, however, contact the tissue depending on (i) the shape and/or other characteristics of the anatomical structure and/or (ii) the orientation of interaction between the tip section 124 and tissue. Therefore, it is often not immediately apparent which combination of the electrodes is best for an operator to pace at any given time, and determining the best combination can be difficult, time-consuming, impractical, and/or error-prone.

To address these concerns and as described in greater detail below with respect to FIGS. 7-10, the system 100 is configured to simultaneously or sequentially deliver stimulating energy to tissue via various combinations of the electrodes on the tip section 124 of the medical device 104 and over a short period of time (e.g., less than the refractory period of the tissue). In some embodiments, the various combinations of electrodes are selected to cover all or a significant portion of the surface area of the tip section 124. In some embodiments, the various combinations of electrodes are selected to include electrodes currently in contact with the tissue (e.g., based, at least in part, on one or more parameter measurements captured, for example, by the sensors 126). In these and still other embodiments, the various combinations of electrodes are selected to include unipolar, bipolar, and/or near-unipolar combinations of electrodes, and/or combinations of electrodes having different sizes.

In this manner, the devices, systems, and associated method of the present technology are configured to pace using several different combinations of electrodes, thereby (i) covering a large number of potential catheter-tissue orientations and interactions and (ii) obviating the practice of an operator selecting an appropriate combination of electrodes and/or applying the selected configuration to the power source or stimulator. In turn, the devices, systems, and associated methods of the present disclosure are expected to provide rapid and accurate identification of tissue that initiates or maintains cardiac arrhythmias and/or to provide rapid and accurate indications of whether nerve tissue is positioned proximate the tip section.

As used herein, electrode combinations are considered bipolar when energy pulses (e.g., voltage and/or current) are applied between electrodes that are closely-spaced relative to one another (e.g., within 10 mm or less of one another), with near-unipolar electrode combinations being bipolar electrode combinations in which one electrode remains spaced away from tissue. Otherwise, electrode combinations are considered unipolar. Voltages, electric fields, and/or current densities in surrounding tissue decay more quickly with distance when using bipolar electrode combinations (e.g. electrodes that are relatively close together), leading to more focused stimulation and reduced excitation of surrounding tissue. Spatial decay also depends on the size and number of electrodes used in each combination, with larger or more spatially-distributed configurations generally leading to stimulation over a larger volume of tissue. Bipolar stimulation with small electrodes (e.g., between two or more of the sensors 126) can be useful for capturing cardiac tissue in a precisely controlled location. The location of stimulation can be precisely controlled if only one of the small electrodes used for stimulation is permitted to contact tissue, for example when energy pulses are applied in a near-unipolar configuration.

2. Three-Dimensional Models of Anatomical Structures

Figure 5:
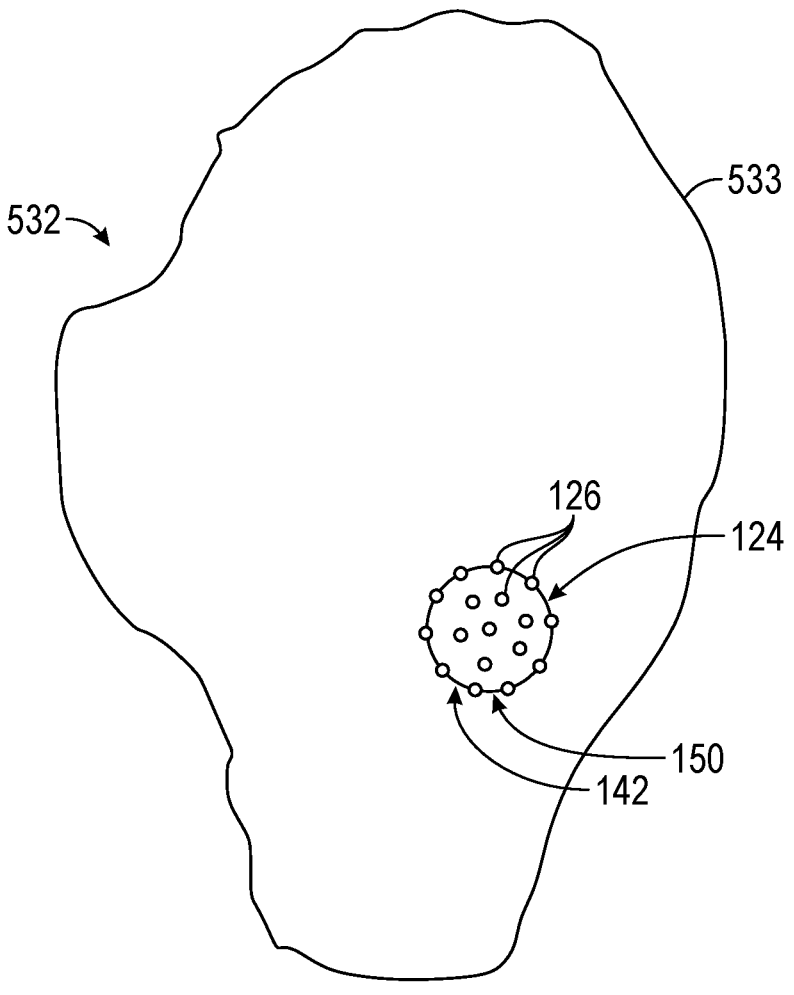
FIG. 5 is a schematic representation of a medical device within an anatomical structure of a patient in accordance with various embodiments of the present technology.

FIG. 5 is a schematic representation of the tip section 124 of the medical device 104 within an anatomical structure 532 (e.g., an anatomical cavity, such as a heart cavity) of the patient 102 in accordance with various embodiments of the present technology. As the deformable portion 142 of the tip section 124 is positioned against tissue of the anatomical structure 532, various portions of the electrode 150 and various one of the sensor 126 contact a blood-tissue boundary surface 533 of the anatomical structure 532. In certain implementations, the delivery of energy from the tip section 124 to tissue of the anatomical structure 532 can rely upon proximity between the tip section 124 and the tissue. In such implementations, it may be particularly desirable for the graphical user interface 110 of FIG. 2 to display a three-dimensional model of the medical device 104 (e.g., of the tip section 124) and/or a three-dimensional representation of the anatomical structure 532 to provide the physician with a visualization of the position of the tip section 124 relative to one or more surfaces 533 representing the anatomical structure 532. It should be further appreciated that the devices, systems, and methods of the present disclosure can be implemented using any number and manner of designs of the medical device 104 that rely upon, or at least derive some benefit from, visualization of the location of the tip section 124 relative to one or more surfaces representing the anatomical structure.

Figure 6:
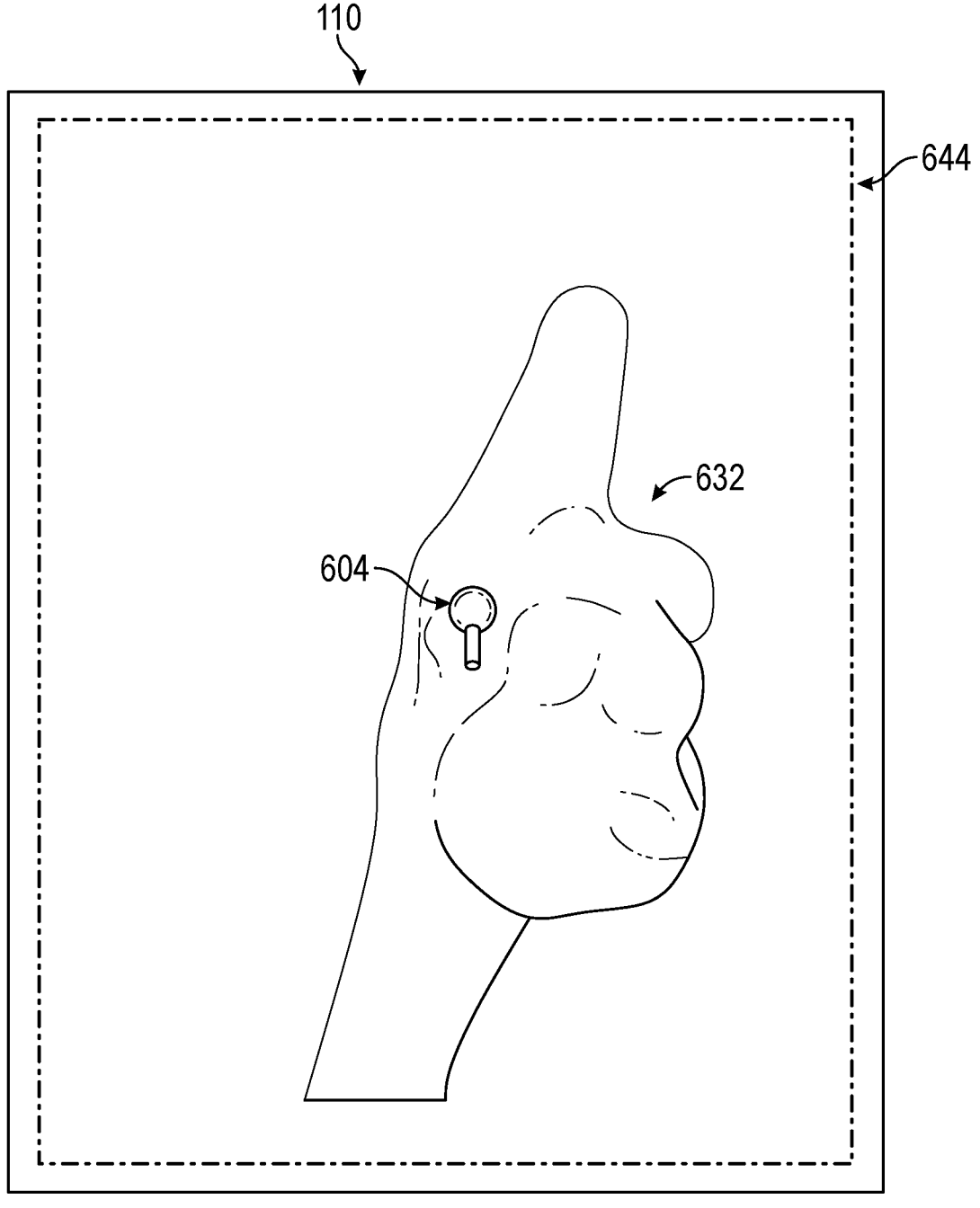
FIG. 6 is a graphical user interface of the system of FIG. 2 displaying a projection of a three-dimensional model during a medical procedure and configured in accordance with various embodiments of the present technology.

FIG. 6 is a graphical user interface 110 of the system of FIG. 2 displaying a projection of a three-dimensional model 644 during a medical procedure and configured in accordance with various embodiments of the present technology. Referring to FIGS. 2-6 together, the model 644 includes a three-dimensional representation 632 (FIG. 6) of the anatomical structure 532 (FIG. 5) constructed based on known positions of the tip section 124 of the medical device 104 in the anatomical structure 532 (e.g., prior to, during, and/or after application of energy to tissue of the anatomical structure 532) and additionally, or alternatively, based on images (e.g., segmented CT or MR images) of the anatomical structure 532 (FIG. 5) acquired prior to or during the procedure. For example, if the tip section 124 of the medical device 104 is movable in blood in the anatomical structure 532 and obstructed only by the surface 533 (FIG. 5) of the anatomical structure 532, the known positions of the tip section 124 of the medical device 104 can be taken together to provide an indication of a blood-tissue boundary of the anatomical structure 532, and this blood-tissue boundary can form a basis for the three-dimensional representation 632 of the anatomical structure 532 shown in FIG. 6. In some embodiments, the three-dimensional representation 632 can be a triangular mesh or non-uniform rational basis spline surface.

In general, the three-dimensional model 644 (FIG. 6) can be projected onto the graphical user interface 110. The three-dimensional model 644 can include the three-dimensional representation 632 of the anatomical structure 532 and/or a representation 604 (FIG. 6) of the medical device 104. The representation 604 of the medical device 104 can include, for example, a depiction of the tip section 124 at a location and orientation determined based on signals received from the sensors 126 (e.g., from a magnetic position sensor and/or other sensors) distributed about the tip section 124. By way of example and not limitation, the representation 604 can include one or more of the following: an icon; an outline; a two-dimensional geometric shape such as a circle; and a three-dimensional geometric shape such as a sphere. Additionally, or alternatively, the representation 604 of the medical device 104 can include a three-dimensional depiction of the tip section 124. Continuing with this example, the three-dimensional representation 604 of the tip section 124 can be at least partially based on knowledge of the size and shape of the tip section 124. Thus, for example, in implementations in which the deformable portion 142 of the tip section 124 is deformed through contact with the surface 533 of an anatomical structure 532, the deformation of the deformable portion 142 can be shown in the three-dimensional representation 604 of the tip section 124 in FIG. 6.

It should be appreciated that the three-dimensional model 644 has utility as, among other things, an analog for the position of the tip section 124 of the medical device 104 in the anatomical structure 532. That is, the position and orientation of the tip section 124 of the medical device 104 relative to the surface 533 of the anatomical structure 532 can be estimated (e.g., based on signals received by the interface unit 108 from the sensors 126, such as from a magnetic position sensor) and can be represented on the graphical user interface 110 at a corresponding position and orientation within the three-dimensional representation 632 of the anatomical structure 532. Thus, for example, as the tip section 124 moves within the anatomical structure 532 during a medical procedure, the representation 604 of the medical device 104 can be depicted on the graphical user interface 110 in FIG. 6 as undergoing analogous, or at least similar, movements relative to the three-dimensional representation 632 of the anatomical structure 532 in the three-dimensional model 644. Given this correspondence between the three-dimensional model 644 and the physical aspects of the medical procedure, it should be appreciated that displaying images of the three-dimensional model 644 on the graphical user interface 110 can be a useful visualization tool for the physician as the physician moves the tip section 124 of the medical device 104 in the anatomical structure 532.

As best seen in FIGS. 5 and 6, in one specific example, the tip section 124 can be placed adjacent to the surface 533 of the anatomical structure 532 and energy (e.g., RF energy, PF energy, electrical energy, stimulating energy, etc.) can be directed from the electrode 150 and/or the sensors 126 of the tip section 124 to the surface 533 of the anatomical structure 532 to pace, diagnose, ablate, or otherwise treat (e.g., deliver reversible electroporation therapy to) tissue at a treatment site. Such diagnosis along the surface 533 of the anatomical structure 532 can include, for example, locating nerve tissue proximate the tip section 124. Additionally, or alternatively, such diagnosis along the surface 533 of the anatomical structure 532 can include, for example, locating cardiac tissue that initiates or maintains a cardiac arrhythmia. In these and other embodiments, such treatment along the surface 533 of the anatomical structure 532 can, for example, treat cardiac arrhythmia in patients with this condition. However, the safety and effectiveness of the lesions created using the tip section 124 along the surface 533 of the anatomical structure 532 can be dependent upon the location of the lesions. Accordingly, the multi-dimensional visualization of the position of the medical device 104 (facilitated by displaying images of the three-dimensional model 644 according to any one or more of the methods described herein) can be useful for the efficient, safe, and/or effective pacing and/or mapping of the heart and/or efficient, safe, and/or effective delivery of ablation treatment to treat cardiac arrhythmia.

US 12,661,518 B2

17

18

3. Associated Methods

Figure 7:
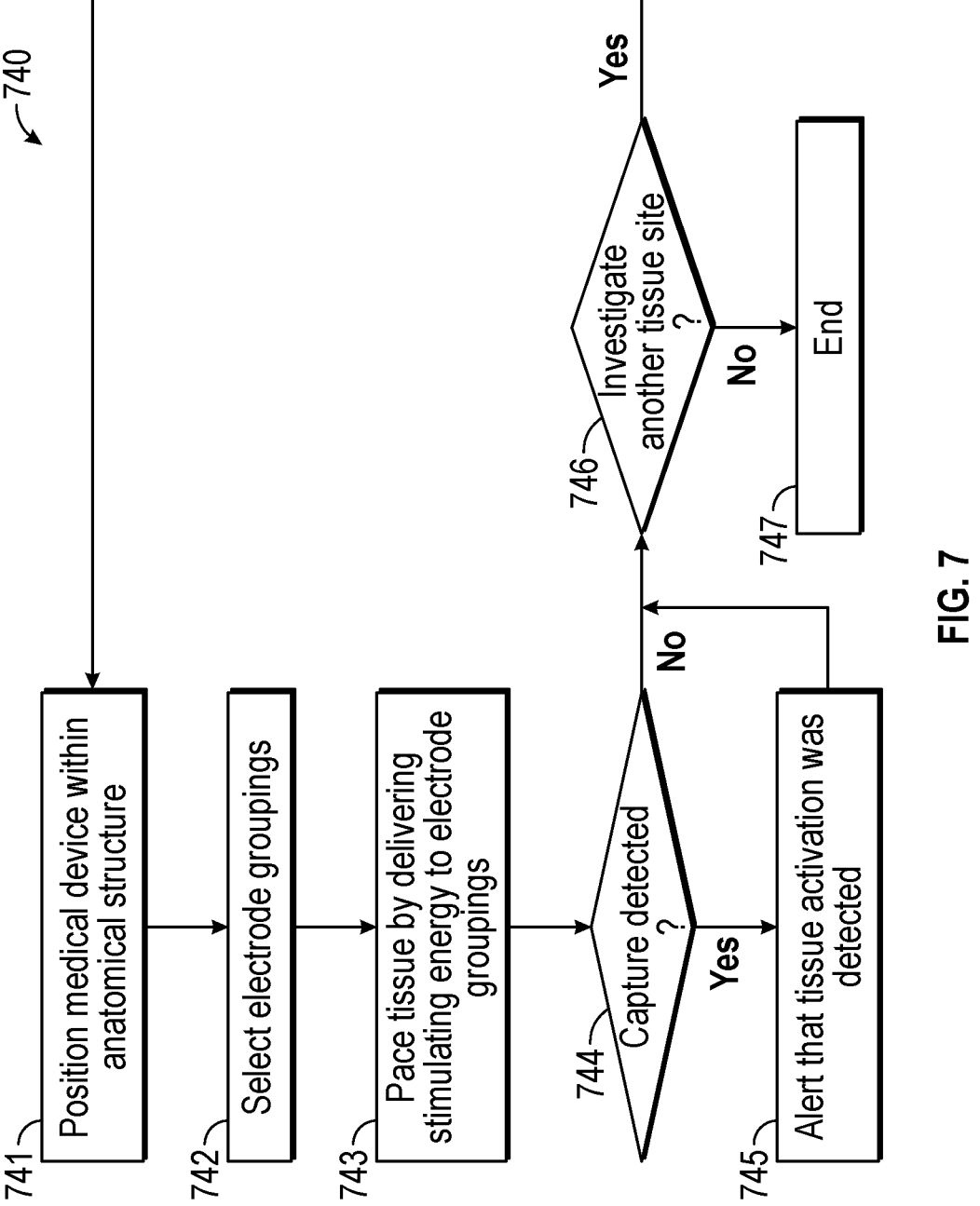
FIG. 7 is a flow diagram illustrating a method for pacing tissue within an anatomical structure in accordance with various embodiments of the present technology.

FIG. 7 illustrates a method 740 for pacing tissue within an anatomical structure of a patient in accordance with various embodiments of the present technology. All or a subset of the steps of the method 740 can be executed by various components or devices of a medical system, such as the system 100 illustrated in FIGS. 2-4 or other suitable systems. For example, all or a subset of the steps of the method 740 can be executed by (i) components or devices of an interface unit (e.g., the interface unit 108) and/or (ii) components or devices of a medical device (e.g., the medical device 104). Furthermore, any one or more of the steps of the method 740 can be executed in accordance with the discussion above.

FIG. 8 is a simplified schematic diagram of a tip section 824 of a medical device 804 configured in accordance with various embodiments of the present technology. As shown, the tip section 824 includes a tip electrode 826t, a center electrode 835, a deformable electrode 850, distal electrodes 826d1-826d4, and proximal electrodes 826p1-826p4. The tip section 824 further includes ring electrodes 851 and 852 positioned on distal end 832 of a shaft 812 of the medical device 804. For the sake of clarity and understanding, FIG. 7 is discussed below in conjunction with FIGS. 8-10.

Referring to FIG. 7, the method 740 begins at block 741 by positioning a medical device within an anatomical structure. In some embodiments, the medical device includes a plurality of electrodes spatially distributed about a tip section of the medical device, similar to the medical device 104 discussed in detail above with respect to FIGS. 2-6. In these and other embodiments, the tip section of the medical device is positioned proximate tissue at a blood-tissue boundary of the anatomical structure. For example, the tip section of the medical device can be positioned proximate or in contact with a potential treatment site within the anatomical structure.

At block 742, the method 740 continues by selecting electrode groupings for tissue stimulation. Referring to FIGS. 7 and 8 together, the method 740 in some embodiments includes placing electrodes into large groupings having multiple source electrodes with one or more common sink electrodes. For example, all or a subset of (a) the distal electrodes 826d1-826d4, the proximal electrodes 826p1-826p4, and/or the tip electrode 826t can be configured as source electrodes and grouped with (b) the center electrode 835 or another electrode configured as a common sink electrode. As described in greater detail below, such a grouping can allow simultaneous delivery of stimulating energy to each of the source electrodes of the group, which can facilitate quickly pacing a majority of the outer surface area of the tip section 824 without added complexity of configuring a generator with relays, switches, or transistors to energize multiple, smaller electrode groupings.

In these and other embodiments, the method 740 includes placing the electrodes into smaller groupings. For example, the method 740 can include grouping various electrodes into pairs. The electrode pairings can be selected to cover a majority of the outer surface area of the tip section 824 to account for multiple orientations at which the tip section 824 can interact with tissue of the anatomical structure. In these and other embodiments, the electrode pairings can be selected to include various unipolar, bipolar, and/or near-unipolar electrode configurations. In these and still other embodiments, the electrode pairings can be selected to primarily include only those electrodes currently in contact with tissue.

FIG. 9 is a table 980 illustrating potential electrode pairings of the tip section 824 of FIG. 8 in accordance with various embodiments of the present technology. As shown, the electrodes of the tip section 824 of the medical device 804 are grouped into the following six pairings, with each pairing having a source electrode and a sink electrode: (1) the deformable electrode 850 and the ring electrode 851; (2) the tip electrode 826t and the center electrode 835; (3) the distal electrode 826d1 and the proximal electrode 826p3; (4) the distal electrode 826d2 and the proximal electrode 826p4; (5) the distal electrode 826d3 and the proximal electrode 826p1; and (6) the distal electrode 826d4 and the proximal electrode 826p2. The electrodes in all but pairing (2) are grouped to provide bipolar energy stimulation, while the electrodes of pairing (2) are grouped to provide near-unipolar energy stimulation. Furthermore, the pairings of electrodes in FIG. 9 are spaced to cover a majority of the outer surface area of the tip section 824 to account for multiple orientations at which the tip section 824 can interact with tissue of the anatomical structure. As described in greater detail below, such groupings can allow sequential delivery of stimulating energy to the electrode pairings, which can facilitate quickly pacing a majority of the outer surface area of the tip section 824 without concern of different electrode impedances or of undesirable combinations of voltages, electric fields, and/or current density in nearby tissue. Although not shown in FIGS. 8 and 9, another potential electrode grouping includes an electrode of the tip section 824 and an electrode patch positioned external to the patient (e.g., to provide unipolar energy stimulation). Still other potential electrode groupings include using an electrode as a source and/or a sink electrode in multiple electrode pairings.

In these and other embodiments, the method 740 can include placing electrodes into groupings based on electrode sizing (e.g., the relative sizes of the electrodes). For example, the method 740 can include grouping two or more electrodes where the source electrode of the group includes an effective surface area much larger than the one or more sink electrodes. As a specific example, the first pairing (1) of FIG. 9 includes the deformable electrode 850 having an effective surface area much larger than the ring electrode 851. Such a pairing allows for the method 740 to address certain mechanical constraints to realize some of the advantages of unipolar energy stimulation while applying bipolar energy stimulation. That is, bipolar energy stimulation has the advantage of delivering more energy over a smaller region of tissue compared to unipolar energy stimulation (e.g., bipolar energy stimulation may have superior spatial decay far from the electrodes used to stimulate tissue). Unipolar energy stimulation, on the other hand, has the advantage of more gradual decay in potential, electric field, and/or current density near the electrodes used to stimulate tissue (e.g., unipolar energy stimulation may have superior spatial decay near the electrodes used to stimulate tissue). Using electrodes with a larger effective surface area can result in more gradual decay near the electrodes used to stimulate tissue, but mechanical constraints (e.g., space) make using two or more of such large electrodes impractical. Thus, by pairing two electrodes where the source electrode of the pair includes an effective surface area much larger than the other electrode, potentials, electric fields, and/or current densities in tissue in the immediate vicinity of the larger source electrode will gradually decay (similar to how they would under unipolar energy stimulation of tissue) except in the areas that are proximate to the smaller electrode. That is, bipolar energy stimulation using two electrodes of different sizes may have superior spatial decay near the larger electrode. This gradual decay is expected to be further enhanced near the larger electrode when the smaller electrode is less likely to be proximate tissue, similar to the ring electrode 851 of FIG. 8. Furthermore, the potentials, electric field, and/or the current densities in tissue far from the electrodes used to stimulate tissue are still expected to decay quickly, maintaining an advantage of bipolar energy stimulation. As a result, such energy stimulation (using two or more electrodes where the source electrode of the group includes an effective surface area much larger than the one or more sink electrodes) can create an electric field that is sufficient to activate nerve tissue proximate the tip section 824 but that is insufficient to activate cardiac tissue proximate the tip section 824.

In these and still other embodiments, the method 740 includes automatically selecting or assisting the selection of electrode groupings. For example, the tip electrode 826*t*, the distal electrodes 826*d*1-826*d*4, and/or the proximal electrodes 826*p*1-826*p*4 of FIG. 8 can be similar to the sensors 126 described in detail above with respect to FIGS. 2-6. In these embodiments, the tip electrode 826*t*, the distal electrodes 826*d*1-826*d*4, and/or the proximal electrodes 826*p*1-826*p*4 can be used to detect which electrodes of the tip section 824 are most likely to be in contact with tissue. For example, the tip electrode 826*t*, the distal electrodes 826*d*1-826*d*4, and/or the proximal electrodes 826*p*1-826*p*4 can be used to generate or measure electrograms, impedances, temperatures, and/or contact forces as described in greater detail above with respect to FIGS. 2-6. Additionally, or alternatively, ultrasound or other visualization techniques can be used to locate one or more of these electrodes relative to tissue. Based, at least in part, on the location of the electrodes relative to tissue and/or on the measurements captured by one or more of the tip electrode 826*t*, the distal electrodes 826*d*1-826*d*4, and/or the proximal electrodes 826*p*1-826*p*4, the method 740 can include automatically selecting and/or suggesting groupings of electrodes. For example, of the electrodes currently in contact with tissue, the method 740 can include automatically selecting and/or suggesting groupings of electrodes to cover a majority of outer surface area of the tip section 824 currently in contact with tissue and/or to include a desired number of bipolar, unipolar, and/or near-unipolar electrode configurations.

As another example, the method 740 can measure one or more signals (e.g., electrograms, impedances, temperatures, contact forces, ultrasound signals) responsive to proximity between the tip section of the medical device and tissue of the anatomical structure. The method 740 can further filter and/or process the one or more signals and determine an ordering (e.g., by sorting and/or applying a threshold) of the one or more signals based at least in part on the measurements, thereby generating an ordering indicative of relative proximity to tissue of the anatomical structure. In some embodiments, the method 740 can display (e.g., on a graphical user interface) one or more configurations for delivery of electrical energy from the tip section of the medical device based at least in part on the ordering. The one or more configurations can be a reduced and/or sorted list of the possible electrode configurations. Thus, the electrode configurations can be reduced and/or sorted based, in part, on the relative proximity between electrodes in the electrode configuration and tissue of the anatomical structure. Additionally, or alternatively, each of the one or more configurations can include a subset of the plurality of electrodes spatially distributed about the tip section of the medical device. To display the one or more configurations, the method 740 can modify a previous display of the one or more configurations (e.g., by changing an order in which the one or more configurations are presented on the display, by changing the one or more configurations based at least in part on the ordering, etc.).

At block 743, the method 740 continues by pacing tissue using the electrode groupings determined at block 742. In particular, the tissue is paced by delivering stimulating energy (e.g., one or more stimulation pulses) to the electrode groupings. In embodiments that include large groupings of electrodes having multiple source electrodes with one or more common sink electrodes, stimulation energy can be driven through the multiple source electrodes simultaneously and return to the common sink electrode(s). If all of the source electrodes are shorted together, however, different electrode impedances will lead to different current passing through each source electrode, thereby applying different amounts of stimulation to tissue through each electrode. As such, the method 740 can include driving the multiple source electrodes simultaneously with multiple high-impedance sources. For example, multiple current sources can be used to drive the source electrodes. As another example, a common voltage can be applied to the source electrodes through a set of series impedances (one set for each source electrode) such that the series impedance is similar to or larger than the impedance of the individual electrode.

Alternatively, stimulation energy (e.g., stimulation pulses) can be driven through groupings of electrodes sequentially (e.g., in a time division multiplexed manner) using relays, transistors, or switches to quickly switch between stimulating the electrode groupings with a generator. Referring to FIG. 9, for example, six stimulation pulses can be driven sequentially through the electrode pairings. The duration of each pulse can be between about 1-20 ms (e.g., approximately 4 ms), and the time required to switch to the next electrode grouping can be about 5 ms (depending on the characteristics of the switching components). Thus, the total duration of a sequence of pulses is provided by the following equation:

$$\text{Total Duration} = (\text{Number of Electrode Groupings})^* \\ (\text{Pulse Duration}) + (\text{Number of Electrode Group-} \\ \text{ings}-1)^*(\text{Switch Duration}) \qquad \text{Equation 1}$$

Continuing with the above example, the total duration of the sequence of pulses driven sequentially through the six electrode groupings of FIG. 9 is between approximately 31-145 ms.

Sequentially driving the electrodes in pairs avoids the problem of different currents passing through each source electrode due to different impedances of the individual electrodes. That is, a single high-impedance source is sufficient to sequentially drive each of the electrode pairings. Moreover, the combined voltage, electric field, and/or current density delivered through tissue when delivering stimulating energy through a sequence of electrode pairings decays more quickly with distance from the electrodes than delivering stimulating energy through multiple source electrodes. As such, the voltages, electric fields, and/or current densities delivered through tissue via each electrode pairing are not expected to interact with or cancel out the voltages, electric fields, and/or current densities delivered through tissue via the other electrode pairings.

Figure 10:
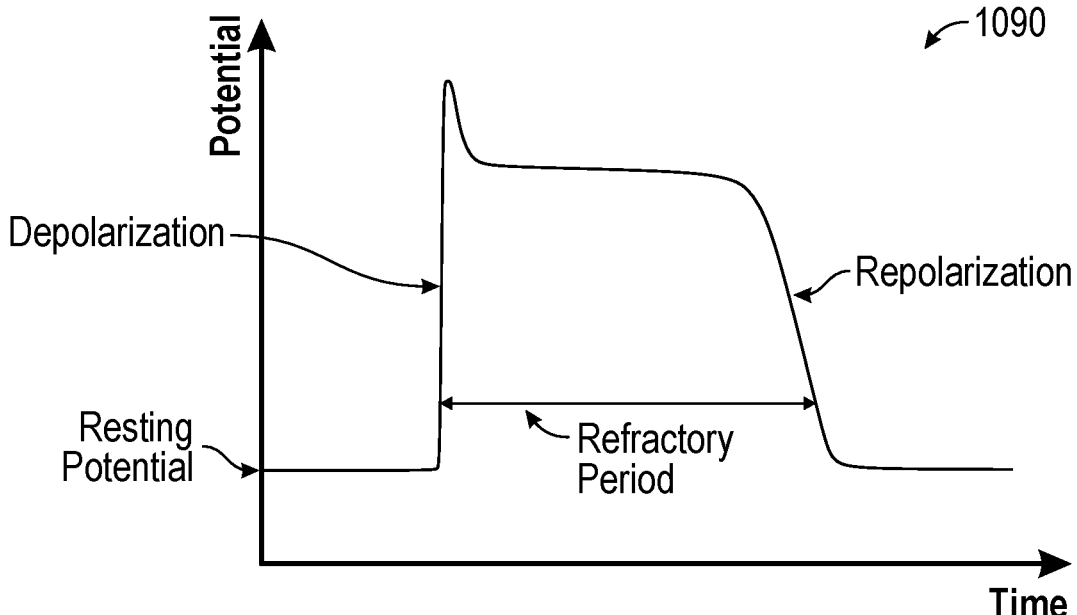
FIG. 10 is a line plot of a cardiac myocyte transmembrane potential measured during an action potential.

Nevertheless, the total duration of the stimulating sequence must be kept short to avoid interaction between stimulations from multiple tissue sites. For example, FIG. 10 is a line plot 1090 of a cardiac myocyte transmembrane potential measured during an action potential, which occurs when the myocyte is activated (e.g., by stimulation). During a refractory period, it may not be possible (or an increased stimulus may be required) to initiate another action potential. The duration of the refractory period of tissue depends on tissue type and on the condition of the tissue, but it is generally greater than 100 ms for human cardiac myocytes. Thus, for electrodes that are closely spaced together (e.g., electrode pairings that are closely spaced together about the tip section 824 of the medical device 804 of FIG. 8), stimulation should take place over a time period well below the refractory period of the stimulated tissue. In other words, the total duration of the stimulating sequence should be less than or equal to 100 ms, preferably less than about 50 ms, to avoid inducing an arrhythmia in the tissue and/or activating the same tissue multiple times in rapid succession.

At block 744, the method 740 continues by determining whether capture (e.g., muscle capture, cardiac tissue capture, etc.) is detected as a result of applying stimulating energy at block 743. Pulsed energy stimulation can activate nearby nerve tissue, thereby causing muscle capture that is observed as patient movement. Thus, in some embodiments, muscle capture can be detected by a physician when the patient moves after applying stimulating energy. In some embodiments, nerve activation and resulting muscle capture can be detected using one or more sensors. For example, sensors positioned at fixed locations on the patient's body and/or location, impedance, and/or imaging sensors can be used to detect muscle capture. In some embodiments, muscle capture can be detected as patient displacement above a fixed threshold within a period of time following energy stimulation. As a specific example of determining whether capture is detected, the method 740 can measure a location of a sensing device (e.g., one or more magnetic field sensors, one or more electrodes, etc.) in a stable position (on the skin of a patient, carried by the medical device, etc.), determine a displacement of the location due to the delivery of electrical energy between two or more electrodes of the tip section of the medical device and/or to or through tissue, and determine whether the displacement is above a fixed threshold or is indicative of capture. If muscle capture is detected at block 744, the method 740 can continue to block 745. Otherwise, the method 740 continues to block 746.

Pulsed energy stimulation can activate nearby cardiac tissue, resulting in activation propagating to other regions of the heart. Cardiac tissue capture can be detected by measuring cardiac signals (e.g. electrograms, electrocardiograms, and/or imaging signals) corresponding to the known location and/or known timing of the delivered pulsed energy stimulation. For example, when pulsed energy stimulation captures nearby cardiac tissue, cardiac signals measured in other regions of the heart and/or on the body surface will typically be synchronized with the pulse delivery, with signal deflections occurring at a consistent delay after each pulse delivery. When pulsed energy stimulation fails to capture nearby cardiac tissue, however, cardiac signals measured in other regions of the heart and/or on the body surface will often not be synchronized with the pulse delivery, with signal deflections occurring instead with a variable delay relative to each pulse delivery. Thus, in some embodiments, cardiac tissue capture can be detected when cardiac signals are synchronized to the pulsed energy stimulation, with a consistent delay. In some embodiments, cardiac tissue capture can be detected as a consistent delay of cardiac signals relative to the pulsed energy stimulation (e.g., signal deflection occurs at the same delay after sequential pulse deliveries, within a fixed margin of error). If cardiac tissue capture is detected at block 744, the method 740 can continue to block 745. Otherwise, the method 740 continues to block 746.

At block 745, the method 740 continues by (e.g., automatically) alerting that tissue activation was detected. In some embodiments, the alerting can include alerting a physician that stimulation delivered at block 743 activated tissue proximate the tip section of the medical device. In these and other embodiments, the alerting can include generating annotations on a three-dimensional representation of the anatomical structure indicating the location of the activated tissue. For example, the method 740 can include displaying one or more visual indicia of electrical activity of the anatomical structure (e.g., of cardiac or nerve tissue) on a graphical user interface. That is, it may be particularly desirable for the method 740 to display one or more annotations or tags alone or in combination with a three-dimensional representation of the anatomical structure and/or a representation of one or more medical devices (e.g., the movable catheter and/or the intracardiac reference) to provide the physician with various information relating to location of activated tissue within the anatomical structure. In these and still other embodiments, if the activated tissue is nerve tissue, the alerting can include preventing delivery of ablative energy at locations corresponding to the activated nerve tissue.

At block 746, the method 740 continues by determining whether to pace or investigate another tissue site. If additional tissue sites remain for investigation, the method 740 can return to block 741 by moving (e.g., dragging, repositioning, reorienting, etc.) the tip section of the catheter to another tissue site. Otherwise, the method 740 can end at block 747.

Although the steps of the method 740 are discussed and illustrated in a particular order, the method 740 illustrated in FIG. 7 is not so limited. In other embodiments, the method 740 can be performed in a different order. In these and other embodiments, any of the steps of the method 740 can be performed before, during, and/or after any of the other steps of the method 740. For example, block 742 in some embodiments can be performed before and/or during block 741. Moreover, a person of ordinary skill in the relevant art will recognize that the illustrated method can be altered and still remain within these and other embodiments of the present technology. For example, one or more steps of the method 740 illustrated in FIG. 7 can be omitted and/or repeated in some embodiments. In these and still other embodiments, one or more steps of the method 740 can be automated.

In some embodiments, the method 740 can include one or more additional steps than illustrated in FIG. 7. For example, in the event that capture is not detected at block 744, the method 740 can further include one or more steps directed to confirming (i) ablation effectiveness, (ii) electrical isolation of patient anatomy (e.g., of a pulmonary vein), and/or (iii) formation of a block across an ablation line. In the context of a cardiac pacing procedure within a ventricle of the heart, the method 740 can further include one or more steps directed to comparing an ECG captured during pacing at a given site to an ECG recorded during a previous arrhythmia episode to determine if the pacing site is a good target ablation site to treat that arrhythmia (e.g. if the ECGs have similar features). As still other examples, the method 740 can include one or more steps directed to achieving a consistent heart rhythm when making an activation map (local activation time or LAT map) and/or directed to entrainment and post-pacing interval (PPI) to determine if a pacing site is part of an arrhythmia circuit.

C. Additional Examples

Several aspects of the present technology are set forth in the following examples.

1. A method for stimulating tissue, the method comprising:

positioning a catheter adjacent tissue within an anatomical structure, wherein the catheter includes two or more electrodes disposed at a distal end thereof;

receiving a request for electrical stimulation of the tissue with the catheter; and based, at least in part, upon the request for electrical stimulation— delivering pulsed electrical energy to a first subset of the two or more electrodes during a first time period, and delivering pulsed electrical energy to a second subset of the two or more electrodes during a second time period, wherein— the second subset is different from the first subset, the second time period does not overlap with the first time period, and a time difference between an end of the first time period and a beginning of the second time period is less than a refractory period of the tissue.

2. The method of example 1 wherein the time difference is less than 20 milliseconds.

3. The method of example 1 wherein the pulsed electrical energy is applied to the tissue.

4. The method of example 1 wherein the pulsed electrical energy is applied through the tissue.

5. The method of example 1 wherein a total duration during which the pulsed electrical energy is applied to or through the tissue is less than or equal to 100 milliseconds.

6. The method of example 1 wherein a total duration during which the pulsed electrical energy is applied to or through the tissue is less than or equal to 50 milliseconds.

7. The method of example 1, further comprising selecting individual ones of the two or more electrodes to include in the first subset and the second subset.

8. The method of example 1 wherein the first subset includes at least one electrode configured as a source electrode and at least one other electrode configured as a sink electrode.

9. The method of example 1 wherein the first subset and/or the second subset include only individual ones of the two or more electrodes currently in contact with the tissue.

10. The method of example 1 wherein the first subset of the two or more electrodes and the second subset of the two or more electrodes span a majority of an effective outer surface area of a tip section of the catheter.

11. The method of example 1 wherein delivering the pulsed electrical energy to the first subset includes simultaneously delivering the pulsed electrical energy to each electrode of the first subset.

12. The method of example 11 wherein simultaneously delivering the pulsed electrical energy includes simultaneously delivering the pulsed electrical energy using two or more current sources.

13. The method of example 11 wherein simultaneously delivering the pulsed electrical energy includes simultaneously delivering the pulsed electrical energy to each electrode of the first subset using a respective series impedance, and wherein each series impedance is similar to or larger than an impedance of a respective electrode.

14. The method of example 1 wherein the first subset and the second subset each include a pair of electrodes, and wherein each pair of electrodes includes at least one electrode not shared by the other pair.

15. The method of example 14 wherein electrodes of at least one of the pairs of electrodes are configured to cooperate to deliver bipolar energy.

16. The method of example 14 or example 15 wherein electrodes of at least one pair are configured to cooperate to deliver near-unipolar energy.

17. The method of example 1 wherein delivering the pulsed electrical energy includes:

using a generator to deliver the pulsed electrical energy to electrodes of the first subset;

using switches, relays, or transistors to electrically couple electrodes in the second subset to the generator after delivering the pulsed electrical energy to the electrodes of the first subset; and using the generator to deliver the pulsed electrical energy to the electrodes of the second subset.

18. The method of example 1 wherein the pulsed electrical energy is sufficient to stimulate the tissue but is insufficient to ablate the tissue.

19. The method of example 1 wherein the pulsed electrical energy is sufficient to stimulate nerve tissue proximate the tip section but is insufficient to stimulate cardiac tissue proximate the tip section.

20. The method of example 1, further comprising detecting capture indicative of activation of the tissue.

21. The method of example 20 wherein the tissue is nerve tissue.

22. The method of example 20 wherein the tissue is cardiac tissue.

23. A method, comprising:

positioning a tip section of a catheter adjacent tissue within an anatomical structure, wherein the tip section includes a two or more electrodes, and wherein a first electrode of the two or more electrodes has a maximum dimension that is at least twice as large as a maximum dimension of a second electrode of the two or more electrodes; and delivering electrical energy between the first and second electrodes.

24. The method of example 23 wherein a distance between the first and second electrodes is less than or equal to 50 mm.

25. The method of example 23 or 24 wherein the first and second electrodes are configured to cooperate to deliver bipolar energy.

26. The method of example 23 wherein the delivering includes applying the electrical energy to the adjacent tissue.

27. The method of any one of examples 23-26 wherein the delivering includes delivering the electrical energy while the second electrode is not in contact with the adjacent tissue.

28. The method of any one of examples 23-27, further comprising configuring at least one electrode of the two or more electrodes as a sink electrode.

29. The method of any of examples 23-28 wherein the electrical energy is sufficient to stimulate tissue proximate the tip section.

30. The method of any of examples 23-29 wherein the electrical energy is insufficient to ablate the adjacent tissue.

31. The method of any one of examples 23-30 wherein the electrical energy is sufficient to stimulate nerve tissue proximate the tip section but is insufficient to stimulate cardiac tissue proximate the tip section.

32. A method for stimulating tissue, the method comprising:

positioning a tip section of a catheter adjacent tissue within an anatomical structure, wherein the tip section is attached to a distal end portion of a catheter shaft, wherein the tip section has a maximum radial dimension that is larger than a maximum radial dimension of the catheter shaft, and further wherein the tip section includes a plurality of electrodes spatially distributed about the tip section;

selecting one or more groupings of individual ones of the plurality of electrodes; and delivering stimulating energy to or through the adjacent tissue via the selected one or more groupings of electrodes, wherein the stimulating energy is sufficient to activate nerve tissue proximate the tip section but is insufficient to ablate or to cause permanent damage to the adjacent tissue.

33. A method, comprising:

receiving a plurality of signals indicative of proximity of a plurality of corresponding electrodes to tissue of an anatomical structure of a patient, wherein electrodes of the plurality of corresponding electrodes are disposed at a distal end of a catheter positioned within the anatomical structure;

determining, based at least in part on the plurality of signals, an ordering indicative of proximity of each of the electrodes to the tissue relative to others of the electrodes;

determining, based at least in part on the ordering, a plurality of possible electrode configurations for delivering electrical energy to the tissue; and causing possible electrode configurations of the plurality of possible electrode configurations to be displayed on a graphical user interface.

34. The method of example 33, further comprising selecting, based at least in part on the ordering, the possible electrode configurations for display on the graphical user interface, wherein the possible electrode configurations represent a reduced list of possible electrode configurations of the plurality of possible electrode configurations.

35. The method of example 33 or example 34, further comprising sorting, based at least in part on the ordering, the possible electrode configurations, wherein causing the possible electrode configurations to be displayed on the graphical user interface includes causing the possible electrode configurations to be displayed on the graphical user interface in an order corresponding to the sorting.

36. The method of any of examples 33-35 wherein each of the possible electrode configurations includes a subset of the electrodes of the plurality of electrodes disposed at the distal end of the catheter.

37. The method of any of examples 33-36, further comprising displaying the possible electrode configurations on the graphical user interface.

38. The method of example 37 wherein displaying the possible electrode configurations includes modifying a previous display of the possible electrode configurations on the graphical user interface.

39. The method of example 38 wherein modifying the previous display includes changing an order in which the possible electrode configurations are presented on the graphical user interface.

40. The method of example 38 or example 39 wherein modifying the previous display includes displaying a different set of possible electrode configurations on the graphical user interface than a previous set of possible electrode configurations displayed on the previous display.

41. The method of any of examples 33-39, further comprising receiving a selection of one or more electrode configurations from the possible electrode configurations.

42. The method of example 41, further comprising delivering electrical energy between electrodes of each of the one or more electrode configurations.

43. The method of example 42 wherein the electrical energy is sufficient to stimulate tissue adjacent the electrodes of each of the one or more electrode configurations.

44. The method of example 42 or example 43 wherein the electrical energy is insufficient to ablate tissue adjacent the electrodes of each of the one or more electrode configurations.

45. The method of any of examples 42-44 wherein the electrical energy is sufficient to stimulate nerve tissue proximate the electrodes of each of the one or more electrode configurations but is insufficient to stimulate cardiac tissue proximate the electrodes of each of the one or more electrode configurations.

D. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference or attached hereto as an Appendix conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A method for stimulating tissue, the method comprising:

positioning a catheter adjacent tissue within an anatomical structure, wherein the catheter includes two or more electrodes disposed at a distal end thereof;

receiving a request for electrical stimulation of the tissue with the catheter; and based, at least in part, upon the request for electrical stimulation-delivering pulsed electrical energy to a first subset of the two or more electrodes during a first time period, and delivering pulsed electrical energy to a second subset of the two or more electrodes during a second time period, wherein— the second subset is different from the first subset, the second time period does not overlap with the first time period, and a time difference between an end of the first time period and a beginning of the second time period is less than a refractory period of the tissue;

detecting capture indicative of activation of the tissue by measuring a displacement of the tissue above a threshold following the delivery of the pulsed electrical energy to the first subset and/or the second subset or by measuring cardiac signals synchronized to the pulsed electrical energy delivered to the first subset and/or the second subset with a consistent delay; and determining that the tissue is nerve tissue if the capture is detected by measuring the displacement above the threshold or that the tissue is cardiac tissue if the capture is detected by measuring the synchronized cardiac signals with the consistent delay.

2. The method of claim 1 wherein the time difference is less than 20 milliseconds.

3. The method of claim 1, further comprising applying pulsed electrical energy delivered to the first subset and/or the second subset through the tissue during the first time period and/or the second time period.

4. The method of claim 1, further comprising applying pulsed electrical energy delivered to the first subset and/or the second subset to or through the tissue during the first time period and/or the second time period, wherein a total duration during which the pulsed electrical energy is applied to or through the tissue over the first and second time periods is less than or equal to 100 milliseconds.

5. The method of claim 1, further comprising applying pulsed electrical energy delivered to the first subset and/or the second subset to or through the tissue during the first time period and/or the second time period, wherein a total duration during which the pulsed electrical energy is applied to or through the tissue over the first and second time periods is less than or equal to 50 milliseconds.

6. The method of claim 1, further comprising selecting individual ones of the two or more electrodes to include in the first subset and the second subset.

7. The method of claim 1 wherein the first subset includes at least one electrode configured as a source electrode and at least one other electrode configured as a sink electrode.

8. The method of claim 1 wherein the first subset and/or the second subset include only individual ones of the two or more electrodes determined to be currently in contact with the tissue based on impedance or electrogram measurements.

9. The method of claim 1 wherein the first subset of the two or more electrodes and the second subset of the two or more electrodes span a majority of an effective outer surface area of a tip section of the catheter.

10. The method of claim 1 wherein delivering the pulsed electrical energy to the first subset includes simultaneously delivering the pulsed electrical energy to each electrode of the first subset.

11. The method of claim 10 wherein simultaneously delivering the pulsed electrical energy includes simultaneously delivering the pulsed electrical energy using two or more current sources.

12. The method of claim 10 wherein simultaneously delivering the pulsed electrical energy includes simultaneously delivering the pulsed electrical energy to each electrode of the first subset using a respective series impedance, and wherein each series impedance is similar to or larger than an impedance of a respective electrode.

13. The method of claim 1 wherein the catheter includes at least three electrodes, and wherein the first subset and the second subset each include a pair of electrodes, and wherein each pair of electrodes includes at least one electrode not shared by the other pair.

14. The method of claim 13 wherein electrodes of at least one of the pairs of electrodes are configured to cooperate to deliver bipolar energy to the tissue.

15. The method of claim 13 wherein electrodes of at least one pair are configured to cooperate to deliver near-unipolar energy to the tissue.

16. The method of claim 1 wherein delivering pulsed electrical energy to the first subset and the second subset includes:

using a generator to deliver the pulsed electrical energy to electrodes of the first subset;

using switches, relays, or transistors to electrically couple electrodes in the second subset to the generator after delivering the pulsed electrical energy to the electrodes of the first subset; and using the generator to deliver the pulsed electrical energy to the electrodes of the second subset.

17. The method of claim 1 wherein pulsed electrical energy delivered to the first subset and/or the second subset is sufficient to stimulate the tissue but is insufficient to ablate the tissue.

18. The method of claim 1 wherein pulsed electrical energy delivered to the first subset and/or the second subset is sufficient to stimulate nerve tissue proximate a tip section of the catheter but is insufficient to stimulate cardiac tissue proximate the tip section of the catheter.

19. The method of claim 1, further comprising detecting capture indicative of activation of the tissue by measuring a displacement of the tissue above a threshold following the deliveries of the pulsed electrical energy.

20. The method of claim 19 wherein the tissue is nerve tissue.

21. The method of claim 19 wherein the tissue is cardiac tissue.

22. A method for determining tissue type within an anatomical structure, the method comprising:

positioning a catheter adjacent tissue within the anatomical structure, wherein the catheter includes two or more electrodes disposed at a deformable tip section thereof;

receiving a request for electrical stimulation of the tissue with the catheter;

based, at least in part, upon the request for electrical stimulation— delivering pulsed electrical energy to a first subset of the two or more electrodes during a first time period, and delivering pulsed electrical energy to a second subset of the two or more electrodes during a second time period;

detecting capture indicative of activation of the tissue by measuring a displacement of the tissue above a threshold following the delivery of the pulsed electrical energy to the first subset and/or the second subset or by measuring cardiac signals synchronized to the pulsed electrical energy delivered to the first subset and/or the second subset with a consistent delay; and determining that the tissue is nerve tissue if the capture is detected by measuring the displacement above the threshold or that the tissue is cardiac tissue if the capture is detected by measuring the synchronized cardiac signals with the consistent delay, wherein— the second subset is different from the first subset, the second time period does not overlap with the first time period, a time difference between an end of the first time period and a beginning of the second time period is less than a refractory period of the tissue, a total duration of the first time period and the second time period is less than or equal to 50 milliseconds, and the pulsed electrical energy is sufficient to stimulate nerve tissue proximate the deformable tip section but is insufficient to stimulate cardiac tissue proximate the deformable tip section.

23. The method of claim 22, further comprising:

displaying, on a graphical user interface, a representation of the catheter within the anatomical structure based on the electrical stimulation.

* * * * *